US009301687B2

(12) United States Patent
Kemp

(10) Patent No.: US 9,301,687 B2
(45) Date of Patent: Apr. 5, 2016

(54) SYSTEM AND METHOD FOR OCT DEPTH CALIBRATION

(71) Applicant: VOLCANO CORPORATION, San Diego, CA (US)

(72) Inventor: Nathaniel J. Kemp, Concord, MA (US)

(73) Assignee: Volcano Corporation, San Diego, CA (US)

( * ) Notice: Subject to any disclaimer, the term of this patent is extended or adjusted under 35 U.S.C. 154(b) by 77 days.

(21) Appl. No.: 14/206,485

(22) Filed: Mar. 12, 2014

(65) Prior Publication Data

US 2014/0270445 A1 Sep. 18, 2014

Related U.S. Application Data

(60) Provisional application No. 61/778,761, filed on Mar. 13, 2013.

(51) Int. Cl.

| | |
|---|---|
| ***G06K 9/00*** | (2006.01) |
| ***A61B 5/00*** | (2006.01) |
| ***A61B 5/02*** | (2006.01) |
| *A61B 6/00* | (2006.01) |

(52) U.S. Cl.

CPC ............. *A61B 5/0073* (2013.01); *A61B 5/0066* (2013.01); *A61B 5/0084* (2013.01); *A61B 5/02007* (2013.01); *A61B 5/6852* (2013.01); *A61B 2560/0223* (2013.01)

(58) Field of Classification Search

CPC ............... A61B 5/00; G06T 7/00; G06K 9/00

USPC ........... 382/128, 129, 130, 131, 132, 13, 134; 378/4, 8, 901, 21–27, 101

See application file for complete search history.

(56) References Cited

U.S. PATENT DOCUMENTS

| | | | |
|---|---|---|---|
| 3,301,258 | A | 1/1967 | Werner |
| 3,617,880 | A | 11/1971 | Cormack et al. |
| 3,789,841 | A | 2/1974 | Antoshkiw |
| 3,841,308 | A | 10/1974 | Tate |
| 4,140,364 | A | 2/1979 | Yamashita et al. |
| 4,274,423 | A | 6/1981 | Mizuno et al. |
| 4,344,438 | A | 8/1982 | Schultz |
| 4,398,791 | A | 8/1983 | Dorsey |

(Continued)

FOREIGN PATENT DOCUMENTS

| | | | |
|---|---|---|---|
| EP | 1041373 | A2 | 10/2000 |
| EP | 01172637 | A1 | 1/2002 |

(Continued)

OTHER PUBLICATIONS

Sihan et al., 2008, A novel approach to quantitative analysis of intraluminal optical coherence tomography imaging, Comput. Cardiol:1089-1092.

(Continued)

*Primary Examiner* — Abolfazl Tabatabai

(74) *Attorney, Agent, or Firm* — Thomas C. Meyers; Brown Rudnick LLP

(57) ABSTRACT

The invention generally relates to methods for calibrating an OCT image by comparing a detected location of a feature within the image to an expected location of the feature, calculating a calibration value, and transforming the location of pixels within the image to provide a calibrated image.

4 Claims, 16 Drawing Sheets

801
433
826
839
859
841

(56) References Cited

U.S. PATENT DOCUMENTS 4,432,370 A 2/1984 Hughes et al.
4,552,554 A 11/1985 Gould et al.
4,577,543 A 3/1986 Wilson
4,676,980 A 6/1987 Segal et al.
4,682,895 A 7/1987 Costello
4,733,665 A 3/1988 Palmaz
4,744,619 A 5/1988 Cameron
4,762,129 A 8/1988 Bonzel
4,766,386 A 8/1988 Oliver et al.
4,771,774 A 9/1988 Simpson et al.
4,794,931 A 1/1989 Yock
4,800,886 A 1/1989 Nestor
4,803,639 A 2/1989 Steele et al.
4,816,567 A 3/1989 Cabilly et al.
4,819,740 A 4/1989 Warrington
4,821,731 A 4/1989 Martinelli et al.
4,824,435 A 4/1989 Giesy et al.
4,830,023 A 5/1989 de Toledo et al.
4,834,093 A 5/1989 Littleford et al.
4,841,977 A 6/1989 Griffith et al.
4,864,578 A 9/1989 Proffitt et al.
4,873,690 A 10/1989 Adams
4,877,314 A 10/1989 Kanamori
4,887,606 A 12/1989 Yock et al.
4,917,085 A 4/1990 Smith
4,917,097 A 4/1990 Proudian et al.
4,928,693 A 5/1990 Goodin et al.
4,932,413 A 6/1990 Shockey et al.
4,932,419 A 6/1990 de Toledo
4,948,229 A 8/1990 Soref
4,951,677 A 8/1990 Crowley et al.
4,969,742 A 11/1990 Falk et al.
4,987,412 A 1/1991 Vaitekunas et al.
4,993,412 A 2/1991 Murphy-Chutorian
4,998,972 A 3/1991 Chin et al.
5,000,185 A 3/1991 Yock
5,024,234 A 6/1991 Leary et al.
5,025,445 A 6/1991 Anderson et al.
5,032,123 A 7/1991 Katz et al.
5,037,169 A 8/1991 Chun
5,039,193 A 8/1991 Snow et al.
5,040,548 A 8/1991 Yock
5,041,108 A 8/1991 Fox et al.
5,054,492 A 10/1991 Scribner et al.
5,065,010 A 11/1991 Knute
5,065,769 A 11/1991 de Toledo
5,085,221 A 2/1992 Ingebrigtsen et al.
5,095,911 A 3/1992 Pomeranz
5,100,424 A 3/1992 Jang et al.
5,120,308 A 6/1992 Hess
5,125,137 A 6/1992 Corl et al.
5,135,486 A 8/1992 Eberle et al.
5,135,516 A 8/1992 Sahatjian et al.
5,155,439 A 10/1992 Holmbo et al.
5,158,548 A 10/1992 Lau et al.
5,163,445 A 11/1992 Christian et al.
5,167,233 A 12/1992 Eberle et al.
5,174,295 A 12/1992 Christian et al.
5,176,141 A 1/1993 Bom et al.
5,176,674 A 1/1993 Hofmann
5,178,159 A 1/1993 Christian
5,183,048 A 2/1993 Eberle
5,188,632 A 2/1993 Goldenberg
5,201,316 A 4/1993 Pomeranz et al.
5,202,745 A 4/1993 Sorin et al.
5,203,779 A 4/1993 Muller et al.
5,220,922 A 6/1993 Barany
5,224,953 A 7/1993 Morgentaler
5,226,421 A 7/1993 Frisbie et al.
5,240,003 A 8/1993 Lancee et al.
5,240,437 A 8/1993 Christian
5,242,460 A 9/1993 Klein et al.
5,243,988 A 9/1993 Sieben et al.
5,257,974 A 11/1993 Cox
5,266,302 A 11/1993 Peyman et al.
5,267,954 A 12/1993 Nita
5,301,001 A 4/1994 Murphy et al.
5,312,425 A 5/1994 Evans et al.
5,313,949 A 5/1994 Yock
5,313,957 A 5/1994 Little
5,319,492 A 6/1994 Dorn et al.
5,321,501 A 6/1994 Swanson et al.
5,325,198 A 6/1994 Hartley et al.
5,336,178 A 8/1994 Kaplan et al.
5,346,689 A 9/1994 Peyman et al.
5,348,017 A 9/1994 Thornton et al.
5,348,481 A 9/1994 Ortiz
5,353,798 A 10/1994 Sieben
5,358,409 A 10/1994 Obara
5,358,478 A 10/1994 Thompson et al.
5,368,037 A 11/1994 Eberle et al.
5,373,845 A 12/1994 Gardineer et al.
5,373,849 A 12/1994 Maroney et al.
5,375,602 A 12/1994 Lancee et al.
5,377,682 A 1/1995 Ueno et al.
5,383,853 A 1/1995 Jung et al.
5,387,193 A 2/1995 Miraki
5,396,328 A 3/1995 Jestel et al.
5,397,355 A 3/1995 Marin et al.
5,405,377 A 4/1995 Cragg
5,411,016 A 5/1995 Kume et al.
5,419,777 A 5/1995 Hofling
5,421,338 A 6/1995 Crowley et al.
5,423,806 A 6/1995 Dale et al.
5,427,118 A 6/1995 Nita et al.
5,431,673 A 7/1995 Summers et al.
5,436,759 A 7/1995 Dijaili et al.
5,439,139 A 8/1995 Brovelli
5,443,457 A 8/1995 Ginn et al.
5,453,575 A 9/1995 O'Donnell et al.
5,456,693 A 10/1995 Conston et al.
5,459,570 A 10/1995 Swanson et al.
5,480,388 A 1/1996 Zadini et al.
5,485,845 A 1/1996 Verdonk et al.
5,492,125 A 2/1996 Kim et al.
5,496,997 A 3/1996 Pope
5,507,761 A 4/1996 Duer
5,512,044 A 4/1996 Duer
5,514,128 A 5/1996 Hillsman et al.
5,529,674 A 6/1996 Hedgcoth
5,541,730 A 7/1996 Chaney
5,546,717 A 8/1996 Penczak et al.
5,546,948 A 8/1996 Hamm et al.
5,565,332 A 10/1996 Hoogenboom et al.
5,573,520 A 11/1996 Schwartz et al.
5,581,638 A 12/1996 Givens et al.
5,586,054 A 12/1996 Jensen et al.
5,592,939 A 1/1997 Martinelli
5,596,079 A 1/1997 Smith et al.
5,598,844 A 2/1997 Diaz et al.
5,609,606 A 3/1997 O'Boyle
5,630,806 A 5/1997 Inagaki et al.
5,651,366 A 7/1997 Liang et al.
5,660,180 A 8/1997 Malinowski et al.
5,667,499 A 9/1997 Welch et al.
5,667,521 A 9/1997 Keown
5,672,877 A 9/1997 Liebig et al.
5,674,232 A 10/1997 Halliburton
5,693,015 A 12/1997 Walker et al.
5,713,848 A 2/1998 Dubrul et al.
5,745,634 A 4/1998 Garrett et al.
5,771,895 A 6/1998 Slager
5,779,731 A 7/1998 Leavitt
5,780,958 A 7/1998 Strugach et al.
5,798,521 A 8/1998 Froggatt
5,800,450 A 9/1998 Lary et al.
5,803,083 A 9/1998 Buck et al.
5,814,061 A 9/1998 Osborne et al.
5,817,025 A 10/1998 Alekseev et al.
5,820,594 A 10/1998 Fontirroche et al.
5,824,520 A 10/1998 Mulligan-Kehoe
5,827,313 A 10/1998 Ream
5,830,222 A 11/1998 Makower
5,848,121 A 12/1998 Gupta et al.

(56) References Cited

U.S. PATENT DOCUMENTS 5,851,464 A 12/1998 Davila et al.
5,857,974 A 1/1999 Eberle et al.
5,872,829 A 2/1999 Wischmann et al.
5,873,835 A 2/1999 Hastings et al.
5,882,722 A 3/1999 Kydd
5,912,764 A 6/1999 Togino
5,916,194 A 6/1999 Jacobsen et al.
5,921,931 A 7/1999 O'Donnell et al.
5,925,055 A 7/1999 Adrian et al.
5,949,929 A 9/1999 Hamm
5,951,586 A 9/1999 Berg et al.
5,974,521 A 10/1999 Akerib
5,976,120 A 11/1999 Chow et al.
5,978,391 A 11/1999 Das et al.
5,997,523 A 12/1999 Jang
6,021,240 A 2/2000 Murphy et al.
6,022,319 A 2/2000 Willard et al.
6,031,071 A 2/2000 Mandeville et al.
6,036,889 A 3/2000 Kydd
6,043,883 A 3/2000 Leckel et al.
6,050,949 A 4/2000 White et al.
6,059,738 A 5/2000 Stoltze et al.
6,068,638 A 5/2000 Makower
6,074,362 A 6/2000 Jang et al.
6,078,831 A 6/2000 Belef et al.
6,080,109 A 6/2000 Baker et al.
6,091,496 A 7/2000 Hill
6,094,591 A 7/2000 Foltz et al.
6,095,976 A 8/2000 Nachtomy et al.
6,097,755 A 8/2000 Guenther, Jr. et al.
6,099,471 A 8/2000 Torp et al.
6,099,549 A 8/2000 Bosma et al.
6,102,938 A 8/2000 Evans et al.
6,106,476 A 8/2000 Corl et al.
6,120,445 A 9/2000 Grunwald
6,123,673 A 9/2000 Eberle et al.
6,134,003 A 10/2000 Tearney et al.
6,139,510 A 10/2000 Palermo
6,141,089 A 10/2000 Thoma et al.
6,146,328 A 11/2000 Chiao et al.
6,148,095 A 11/2000 Prause et al.
6,151,433 A 11/2000 Dower et al.
6,152,877 A 11/2000 Masters
6,152,878 A 11/2000 Nachtomy et al.
6,159,225 A 12/2000 Makower
6,165,127 A 12/2000 Crowley
6,176,842 B1 1/2001 Tachibana et al.
6,179,809 B1 1/2001 Khairkhahan et al.
6,186,949 B1 2/2001 Hatfield et al.
6,190,353 B1 2/2001 Makower et al.
6,200,266 B1 3/2001 Shokrollahi et al.
6,200,268 B1 3/2001 Vince et al.
6,203,537 B1 3/2001 Adrian
6,208,415 B1 3/2001 De Boer et al.
6,210,332 B1 4/2001 Chiao et al.
6,210,339 B1 4/2001 Kiepen et al.
6,212,308 B1 4/2001 Donald
6,231,518 B1 5/2001 Grabek et al.
6,245,066 B1 6/2001 Morgan et al.
6,249,076 B1 6/2001 Madden et al.
6,254,543 B1 7/2001 Grunwald et al.
6,256,090 B1 7/2001 Chen et al.
6,258,052 B1 7/2001 Milo
6,261,246 B1 7/2001 Pantages et al.
6,275,628 B1 8/2001 Jones et al.
6,283,921 B1 9/2001 Nix et al.
6,283,951 B1 9/2001 Flaherty et al.
6,295,308 B1 9/2001 Zah
6,299,622 B1 10/2001 Snow et al.
6,312,384 B1 11/2001 Chiao
6,325,797 B1 12/2001 Stewart et al.
6,328,696 B1 12/2001 Fraser
6,343,168 B1 1/2002 Murphy et al.
6,343,178 B1 1/2002 Burns et al.
6,350,240 B1 2/2002 Song et al.
6,364,841 B1 4/2002 White et al.
6,366,722 B1 4/2002 Murphy et al.
6,367,984 B1 4/2002 Stephenson et al.
6,373,970 B1 4/2002 Dong et al.
6,375,615 B1 4/2002 Flaherty et al.
6,375,618 B1 4/2002 Chiao et al.
6,375,628 B1 4/2002 Zadno-Azizi et al.
6,376,830 B1 4/2002 Froggatt et al.
6,379,352 B1 4/2002 Reynolds et al.
6,381,350 B1 4/2002 Klingensmith et al.
6,387,124 B1 5/2002 Buscemi et al.
6,396,976 B1 5/2002 Little et al.
6,398,792 B1 6/2002 O'Connor
6,417,948 B1 7/2002 Chowdhury et al.
6,419,644 B1 7/2002 White et al.
6,421,164 B2 7/2002 Tearney et al.
6,423,012 B1 7/2002 Kato et al.
6,426,796 B1 7/2002 Pulliam et al.
6,428,041 B1 8/2002 Wohllebe et al.
6,428,498 B2 8/2002 Uflacker
6,429,421 B1 8/2002 Meller et al.
6,440,077 B1 8/2002 Jung et al.
6,443,903 B1 9/2002 White et al.
6,450,964 B1 9/2002 Webler
6,457,365 B1 10/2002 Stephens et al.
6,459,844 B1 10/2002 Pan
6,468,290 B1 10/2002 Weldon et al.
6,475,149 B1 11/2002 Sumanaweera
6,480,285 B1 11/2002 Hill
6,491,631 B2 12/2002 Chiao et al.
6,491,636 B2 12/2002 Chenal et al.
6,501,551 B1 12/2002 Tearney et al.
6,504,286 B1 1/2003 Porat et al.
6,508,824 B1 1/2003 Flaherty et al.
6,514,237 B1 2/2003 Maseda
6,520,269 B2 2/2003 Geiger et al.
6,520,677 B2 2/2003 Iizuka
6,535,764 B2 3/2003 Imran et al.
6,538,778 B1 3/2003 Leckel et al.
6,544,217 B1 4/2003 Gulachenski
6,544,230 B1 4/2003 Flaherty et al.
6,545,760 B1 4/2003 Froggatt et al.
6,546,272 B1 4/2003 MacKinnon et al.
6,551,250 B2 4/2003 Khalil
6,566,648 B1 5/2003 Froggatt
6,570,894 B2 5/2003 Anderson
6,572,555 B2 6/2003 White et al.
6,579,311 B1 6/2003 Makower
6,584,335 B1 6/2003 Haar et al.
6,592,612 B1 7/2003 Samson et al.
6,594,448 B2 7/2003 Herman et al.
6,602,241 B2 8/2003 Makower et al.
6,611,322 B1 8/2003 Nakayama et al.
6,611,720 B2 8/2003 Hata et al.
6,612,992 B1 9/2003 Hossack et al.
6,615,062 B2 9/2003 Ryan et al.
6,615,072 B1 9/2003 Izatt et al.
6,621,562 B2 9/2003 Durston
6,631,284 B2 10/2003 Nutt et al.
6,638,227 B2 10/2003 Bae
6,645,152 B1 11/2003 Jung et al.
6,646,745 B2 11/2003 Verma et al.
6,655,386 B1 12/2003 Makower et al.
6,659,957 B1 12/2003 Vardi et al.
6,660,024 B1 12/2003 Flaherty et al.
6,663,565 B2 12/2003 Kawagishi et al.
6,665,456 B2 12/2003 Dave et al.
6,669,716 B1 12/2003 Gilson et al.
6,671,055 B1 12/2003 Wavering et al.
6,673,015 B1 1/2004 Glover et al.
6,673,064 B1 1/2004 Rentrop
6,685,648 B2 2/2004 Flaherty et al.
6,689,056 B1 2/2004 Kilcoyne et al.
6,689,144 B2 2/2004 Gerberding
6,696,173 B1 2/2004 Naundorf et al.
6,701,044 B2 3/2004 Arbore et al.
6,701,176 B1 3/2004 Halperin et al.
6,709,444 B1 3/2004 Makower
6,712,836 B1 3/2004 Berg et al.

(56) References Cited

U.S. PATENT DOCUMENTS 6,714,703 B2 3/2004 Lee et al.
6,719,717 B1 4/2004 Johnson et al.
6,725,073 B1 4/2004 Motamedi et al.
6,726,677 B1 4/2004 Flaherty et al.
6,730,107 B2 5/2004 Kelley et al.
6,733,474 B2 5/2004 Kusleika
6,738,144 B1 5/2004 Dogariu
6,740,113 B2 5/2004 Vrba
6,746,464 B1 6/2004 Makower
6,780,157 B2 8/2004 Stephens et al.
6,795,188 B2 9/2004 Ruck et al.
6,795,196 B2 9/2004 Funakawa
6,798,522 B2 9/2004 Stolte et al.
6,822,798 B2 11/2004 Wu et al.
6,830,559 B2 12/2004 Schock
6,832,024 B2 12/2004 Gerstenberger et al.
6,842,639 B1 1/2005 Winston et al.
6,847,449 B2 1/2005 Bashkansky et al.
6,855,115 B2 2/2005 Fonseca et al.
6,856,138 B2 2/2005 Bohley
6,856,400 B1 2/2005 Froggatt
6,856,472 B2 2/2005 Herman et al.
6,860,867 B2 3/2005 Seward et al.
6,866,670 B2 3/2005 Rabiner et al.
6,878,113 B2 4/2005 Miwa et al.
6,886,411 B2 5/2005 Kjellman et al.
6,891,984 B2 5/2005 Petersen et al.
6,895,106 B2 5/2005 Wang et al.
6,898,337 B2 5/2005 Averett et al.
6,900,897 B2 5/2005 Froggatt
6,912,051 B2 6/2005 Jensen
6,916,329 B1 7/2005 Zhao
6,922,498 B2 7/2005 Shah
6,937,346 B2 8/2005 Nebendahl et al.
6,937,696 B1 8/2005 Mostafavi
6,943,939 B1 9/2005 DiJaili et al.
6,947,147 B2 9/2005 Motamedi et al.
6,947,787 B2 9/2005 Webler
6,949,094 B2 9/2005 Yaron
6,952,603 B2 10/2005 Gerber et al.
6,954,737 B2 10/2005 Kalantar et al.
6,958,042 B2 10/2005 Honda
6,961,123 B1 11/2005 Wang et al.
6,966,891 B2 11/2005 Ookubo et al.
6,969,293 B2 11/2005 Thai
6,969,395 B2 11/2005 Eskuri
6,985,234 B2 1/2006 Anderson
7,004,963 B2 2/2006 Wang et al.
7,006,231 B2 2/2006 Ostrovsky et al.
7,010,458 B2 3/2006 Wilt
7,024,025 B2 4/2006 Sathyanarayana
7,027,211 B1 4/2006 Ruffa
7,027,743 B1 4/2006 Tucker et al.
7,033,347 B2 4/2006 Appling
7,035,484 B2 4/2006 Silberberg et al.
7,037,269 B2 5/2006 Nix et al.
7,042,573 B2 5/2006 Froggatt
7,044,915 B2 5/2006 White et al.
7,044,964 B2 5/2006 Jang et al.
7,048,711 B2 5/2006 Rosenman et al.
7,049,306 B2 5/2006 Konradi et al.
7,058,239 B2 6/2006 Singh et al.
7,060,033 B2 6/2006 White et al.
7,060,421 B2 6/2006 Naundorf et al.
7,063,679 B2 6/2006 Maguire et al.
7,068,852 B2 6/2006 Braica
7,074,188 B2 7/2006 Nair et al.
7,095,493 B2 8/2006 Harres
7,110,119 B2 9/2006 Maestle
7,113,875 B2 9/2006 Terashima et al.
7,123,777 B2 10/2006 Rondinelli et al.
7,130,054 B2 10/2006 Ostrovsky et al.
7,139,440 B2 11/2006 Rondinelli et al.
7,153,299 B1 12/2006 Tu et al.
7,171,078 B2 1/2007 Sasaki et al.
7,175,597 B2 2/2007 Vince et al.
7,177,491 B2 2/2007 Dave et al.
7,190,464 B2 3/2007 Alphonse
7,215,802 B2 5/2007 Klingensmith et al.
7,218,811 B2 5/2007 Shigenaga et al.
7,236,812 B1 6/2007 Ballerstadt et al.
7,245,125 B2 7/2007 Harer et al.
7,245,789 B2 7/2007 Bates et al.
7,249,357 B2 7/2007 Landman et al.
7,291,146 B2 11/2007 Steinke et al.
7,292,715 B2 11/2007 Furnish
7,292,885 B2 11/2007 Scott et al.
7,294,124 B2 11/2007 Eidenschink
7,300,460 B2 11/2007 Levine et al.
7,335,161 B2 2/2008 Von Arx et al.
7,337,079 B2 2/2008 Park et al.
7,355,716 B2 4/2008 de Boer et al.
7,356,367 B2 4/2008 Liang et al.
7,358,921 B2 4/2008 Snyder et al.
7,359,062 B2 4/2008 Chen et al.
7,359,554 B2 4/2008 Klingensmith et al.
7,363,927 B2 4/2008 Ravikumar
7,366,376 B2 4/2008 Shishkov et al.
7,382,949 B2 6/2008 Bouma et al.
7,387,636 B2 6/2008 Cohn et al.
7,391,520 B2 6/2008 Zhou et al.
7,397,935 B2 7/2008 Kimmel et al.
7,399,095 B2 7/2008 Rondinelli
7,408,648 B2 8/2008 Kleen et al.
7,414,779 B2 8/2008 Huber et al.
7,440,087 B2 10/2008 Froggatt et al.
7,447,388 B2 11/2008 Bates et al.
7,449,821 B2 11/2008 Dausch
7,450,165 B2 11/2008 Ahiska
RE40,608 E 12/2008 Glover et al.
7,458,967 B2 12/2008 Appling et al.
7,463,362 B2 12/2008 Lasker et al.
7,463,759 B2 12/2008 Klingensmith et al.
7,491,226 B2 2/2009 Palmaz et al.
7,515,276 B2 4/2009 Froggatt et al.
7,527,594 B2 5/2009 Vardi et al.
7,534,251 B2 5/2009 WasDyke
7,535,797 B2 5/2009 Peng et al.
7,547,304 B2 6/2009 Johnson
7,564,949 B2 7/2009 Sattler et al.
7,577,471 B2 8/2009 Camus et al.
7,583,857 B2 9/2009 Xu et al.
7,603,165 B2 10/2009 Townsend et al.
7,612,773 B2 11/2009 Magnin et al.
7,633,627 B2 12/2009 Choma et al.
7,645,229 B2 1/2010 Armstrong
7,658,715 B2 2/2010 Park et al.
7,660,452 B2 2/2010 Zwirn et al.
7,660,492 B2 2/2010 Bates et al.
7,666,204 B2 2/2010 Thornton et al.
7,672,790 B2 3/2010 McGraw et al.
7,680,247 B2 3/2010 Atzinger et al.
7,684,991 B2 3/2010 Stohr et al.
7,711,413 B2 5/2010 Feldman et al.
7,720,322 B2 5/2010 Prisco
7,728,986 B2 6/2010 Lasker et al.
7,734,009 B2 6/2010 Brunner et al.
7,736,317 B2 6/2010 Stephens et al.
7,742,795 B2 6/2010 Stone et al.
7,743,189 B2 6/2010 Brown et al.
7,762,954 B2 7/2010 Nix et al.
7,766,896 B2 8/2010 Kornkven Volk et al.
7,773,792 B2 8/2010 Kimmel et al.
7,775,981 B1 8/2010 Guracar et al.
7,777,399 B2 8/2010 Eidenschink et al.
7,781,724 B2 8/2010 Childers et al.
7,783,337 B2 8/2010 Feldman et al.
7,787,127 B2 8/2010 Galle et al.
7,792,342 B2 9/2010 Barbu et al.
7,801,343 B2 9/2010 Unal et al.
7,801,590 B2 9/2010 Feldman et al.
7,813,609 B2 10/2010 Petersen et al.
7,831,081 B2 11/2010 Li
7,846,101 B2 12/2010 Eberle et al.

(56) References Cited

U.S. PATENT DOCUMENTS 7,853,104 B2 12/2010 Oota et al.
7,853,316 B2 12/2010 Milner et al.
7,860,555 B2 12/2010 Saadat
7,862,508 B2 1/2011 Davies et al.
7,872,759 B2 1/2011 Tearney et al.
7,880,868 B2 2/2011 Aoki
7,881,763 B2 2/2011 Brauker et al.
7,909,844 B2 3/2011 Alkhatib et al.
7,921,854 B2 4/2011 Hennings et al.
7,927,784 B2 4/2011 Simpson
7,929,148 B2 * 4/2011 Kemp ................ G01B 9/02004 356/479
7,930,014 B2 4/2011 Huennekens et al.
7,930,104 B2 4/2011 Baker et al.
7,936,462 B2 5/2011 Jiang et al.
7,942,852 B2 5/2011 Mas et al.
7,947,012 B2 5/2011 Spurchise et al.
7,951,186 B2 5/2011 Eidenschink et al.
7,952,719 B2 5/2011 Brennan, III
7,972,353 B2 7/2011 Hendriksen et al.
7,976,492 B2 7/2011 Brauker et al.
7,977,950 B2 7/2011 Maslen
7,978,916 B2 7/2011 Klingensmith et al.
7,981,041 B2 7/2011 McGahan
7,981,151 B2 7/2011 Rowe
7,983,737 B2 7/2011 Feldman et al.
7,993,333 B2 8/2011 Oral et al.
7,995,210 B2 8/2011 Tearney et al.
7,996,060 B2 8/2011 Trofimov et al.
7,999,938 B2 8/2011 Wang
8,021,377 B2 9/2011 Eskuri
8,021,420 B2 9/2011 Dolan
8,036,732 B2 10/2011 Milner
8,040,586 B2 10/2011 Smith et al.
8,047,996 B2 11/2011 Goodnow et al.
8,049,900 B2 11/2011 Kemp et al.
8,050,478 B2 11/2011 Li et al.
8,050,523 B2 11/2011 Younge et al.
8,052,605 B2 11/2011 Muller et al.
8,057,394 B2 11/2011 Dala-Krishna
8,059,923 B2 11/2011 Bates et al.
8,070,800 B2 12/2011 Lock et al.
8,080,800 B2 12/2011 Hoctor et al.
8,088,102 B2 1/2012 Adams et al.
8,100,838 B2 1/2012 Wright et al.
8,104,479 B2 1/2012 Glynn et al.
8,108,030 B2 1/2012 Castella et al.
8,114,102 B2 2/2012 Galdonik et al.
8,116,605 B2 2/2012 Petersen et al.
8,125,648 B2 2/2012 Milner et al.
8,126,239 B2 2/2012 Sun et al.
8,133,199 B2 3/2012 Weber et al.
8,133,269 B2 3/2012 Flechsenhar et al.
8,140,708 B2 3/2012 Zaharia et al.
8,148,877 B2 4/2012 Jiang et al.
8,167,932 B2 5/2012 Bourang et al.
8,172,757 B2 5/2012 Jaffe et al.
8,177,809 B2 5/2012 Mavani et al.
8,187,191 B2 5/2012 Hancock et al.
8,187,267 B2 5/2012 Pappone et al.
8,187,830 B2 5/2012 Hu et al.
8,199,218 B2 6/2012 Lee et al.
8,206,429 B2 6/2012 Gregorich et al.
8,208,995 B2 6/2012 Tearney et al.
8,222,906 B2 7/2012 Wyar et al.
8,233,681 B2 7/2012 Aylward et al.
8,233,718 B2 7/2012 Klingensmith et al.
8,238,624 B2 8/2012 Doi et al.
8,239,938 B2 8/2012 Simeral et al.
8,277,386 B2 10/2012 Ahmed et al.
8,280,470 B2 10/2012 Milner et al.
8,289,284 B2 10/2012 Glynn et al.
8,289,522 B2 10/2012 Tearney et al.
8,298,147 B2 10/2012 Huennekens et al.
8,298,149 B2 10/2012 Hastings et al.
8,301,000 B2 10/2012 Sillard et al.
8,309,428 B2 11/2012 Lemmerhirt et al.
8,317,713 B2 11/2012 Davies et al.
8,323,201 B2 12/2012 Towfiq et al.
8,329,053 B2 12/2012 Martin et al.
8,336,643 B2 12/2012 Harleman
8,349,000 B2 1/2013 Schreck
8,353,945 B2 1/2013 Andreas et al.
8,353,954 B2 1/2013 Cai et al.
8,357,981 B2 1/2013 Martin et al.
8,361,097 B2 1/2013 Patel et al.
8,386,560 B2 2/2013 Ma et al.
8,398,591 B2 3/2013 Mas et al.
8,412,312 B2 4/2013 Judell et al.
8,417,491 B2 4/2013 Trovato et al.
8,449,465 B2 5/2013 Nair et al.
8,454,685 B2 6/2013 Hariton et al.
8,454,686 B2 6/2013 Alkhatib
8,475,522 B2 7/2013 Jimenez et al.
8,478,384 B2 7/2013 Schmitt et al.
8,486,062 B2 7/2013 Belhe et al.
8,486,063 B2 7/2013 Werneth et al.
8,491,567 B2 7/2013 Magnin et al.
8,500,798 B2 8/2013 Rowe et al.
8,550,911 B2 10/2013 Sylla
8,594,757 B2 * 11/2013 Boppart ................ A61B 3/102 600/160
8,597,349 B2 12/2013 Alkhatib
8,600,477 B2 12/2013 Beyar et al.
8,600,917 B1 12/2013 Schimert et al.
8,601,056 B2 12/2013 Lauwers et al.
8,620,055 B2 12/2013 Barratt et al.
8,644,910 B2 * 2/2014 Rousso ............. A61B 5/02755 250/370.09
2001/0007940 A1 7/2001 Tu et al.
2001/0029337 A1 10/2001 Pantages et al.
2001/0037073 A1 11/2001 White et al.
2001/0046345 A1 11/2001 Snyder et al.
2001/0049548 A1 12/2001 Vardi et al.
2002/0034276 A1 3/2002 Hu et al.
2002/0041723 A1 4/2002 Ronnekleiv et al.
2002/0069676 A1 6/2002 Kopp et al.
2002/0089335 A1 7/2002 Williams
2002/0099289 A1 7/2002 Crowley
2002/0163646 A1 11/2002 Anderson
2002/0186818 A1 12/2002 Arnaud et al.
2002/0196446 A1 12/2002 Roth et al.
2002/0197456 A1 12/2002 Pope
2003/0004412 A1 1/2003 Izatt et al.
2003/0016604 A1 1/2003 Hanes
2003/0018273 A1 1/2003 Corl et al.
2003/0023153 A1 1/2003 Izatt et al.
2003/0032886 A1 2/2003 Dgany et al.
2003/0050871 A1 3/2003 Broughton
2003/0065371 A1 4/2003 Satake
2003/0069723 A1 4/2003 Hegde
2003/0077043 A1 4/2003 Hamm et al.
2003/0085635 A1 5/2003 Davidsen
2003/0090753 A1 5/2003 Takeyama et al.
2003/0092995 A1 5/2003 Thompson
2003/0093059 A1 5/2003 Griffin et al.
2003/0103212 A1 6/2003 Westphal et al.
2003/0152259 A1 8/2003 Belykh et al.
2003/0181802 A1 9/2003 Ogawa
2003/0187369 A1 10/2003 Lewis et al.
2003/0194165 A1 10/2003 Silberberg et al.
2003/0195419 A1 10/2003 Harada
2003/0208116 A1 11/2003 Liang et al.
2003/0212491 A1 11/2003 Mitchell et al.
2003/0219202 A1 11/2003 Loeb et al.
2003/0220749 A1 11/2003 Chen et al.
2003/0228039 A1 12/2003 Green
2004/0015065 A1 1/2004 Panescu et al.
2004/0023317 A1 2/2004 Motamedi et al.
2004/0028333 A1 2/2004 Lomas
2004/0037742 A1 2/2004 Jen et al.
2004/0042066 A1 3/2004 Kinoshita et al.
2004/0054287 A1 3/2004 Stephens
2004/0067000 A1 4/2004 Bates et al.

(56) References Cited

U.S. PATENT DOCUMENTS

2004/0068161 A1 4/2004 Couvillon
2004/0082844 A1 4/2004 Vardi et al.
2004/0092830 A1 5/2004 Scott et al.
2004/0106853 A1 6/2004 Moriyama
2004/0111552 A1 6/2004 Arimilli et al.
2004/0126048 A1 7/2004 Dave et al.
2004/0143160 A1 7/2004 Couvillon
2004/0146546 A1 7/2004 Gravett et al.
2004/0186369 A1 9/2004 Lam
2004/0186558 A1 9/2004 Pavcnik et al.
2004/0195512 A1 10/2004 Crosetto
2004/0220606 A1 11/2004 Goshgarian
2004/0225220 A1 11/2004 Rich
2004/0239938 A1 12/2004 Izatt
2004/0242990 A1 12/2004 Brister et al.
2004/0248439 A1 12/2004 Gernhardt et al.
2004/0260236 A1 12/2004 Manning et al.
2005/0013778 A1 1/2005 Green et al.
2005/0031176 A1 2/2005 Hertel et al.
2005/0036150 A1 2/2005 Izatt et al.
2005/0078317 A1 4/2005 Law et al.
2005/0101859 A1 5/2005 Maschke
2005/0140582 A1 6/2005 Lee et al.
2005/0140682 A1 6/2005 Sumanaweera et al.
2005/0140981 A1 6/2005 Waelti
2005/0140984 A1 6/2005 Hitzenberger
2005/0147303 A1 7/2005 Zhou et al.
2005/0165439 A1 7/2005 Weber et al.
2005/0171433 A1 8/2005 Boppart et al.
2005/0171438 A1 8/2005 Chen et al.
2005/0182297 A1 8/2005 Gravenstein et al.
2005/0196028 A1 9/2005 Kleen et al.
2005/0197585 A1 9/2005 Brockway et al.
2005/0213103 A1 9/2005 Everett et al.
2005/0215942 A1 9/2005 Abrahamson et al.
2005/0234445 A1 10/2005 Conquergood et al.
2005/0243322 A1 11/2005 Lasker et al.
2005/0249391 A1 11/2005 Kimmel et al.
2005/0251567 A1 11/2005 Ballew et al.
2005/0254059 A1 11/2005 Alphonse
2005/0264823 A1 12/2005 Zhu et al.
2006/0013523 A1 1/2006 Childlers et al.
2006/0015126 A1 1/2006 Sher
2006/0029634 A1 2/2006 Berg et al.
2006/0036167 A1 2/2006 Shina
2006/0038115 A1 2/2006 Maas
2006/0039004 A1 2/2006 de Boer et al.
2006/0041180 A1 2/2006 Viswanathan et al.
2006/0045536 A1 3/2006 Arahira
2006/0055936 A1 3/2006 Yun et al.
2006/0058622 A1 3/2006 Tearney et al.
2006/0064009 A1 3/2006 Webler et al.
2006/0067620 A1 3/2006 Shishkov et al.
2006/0072808 A1 4/2006 Grimm et al.
2006/0074442 A1 4/2006 Noriega et al.
2006/0098927 A1 5/2006 Schmidt et al.
2006/0100694 A1 5/2006 Globerman
2006/0106375 A1 5/2006 Werneth et al.
2006/0132790 A1 6/2006 Gutin
2006/0135870 A1 6/2006 Webler
2006/0142703 A1 6/2006 Carter et al.
2006/0142733 A1 6/2006 Forsberg
2006/0173299 A1 8/2006 Romley et al.
2006/0179255 A1 8/2006 Yamazaki
2006/0184048 A1 8/2006 Saadat
2006/0187537 A1 8/2006 Huber et al.
2006/0195269 A1 8/2006 Yeatman et al.
2006/0204119 A1 9/2006 Feng et al.
2006/0229591 A1 10/2006 Lee
2006/0239312 A1 10/2006 Kewitsch et al.
2006/0241342 A1 10/2006 Macaulay et al.
2006/0241465 A1 10/2006 Huennekens et al.
2006/0241503 A1 10/2006 Schmitt et al.
2006/0244973 A1 11/2006 Yun et al.
2006/0258895 A1 11/2006 Maschke
2006/0264743 A1 11/2006 Kleen et al.
2006/0267756 A1 11/2006 Kates
2006/0270976 A1 11/2006 Savage et al.
2006/0276709 A1 12/2006 Khamene et al.
2006/0279742 A1 12/2006 Tearney et al.
2006/0279743 A1 12/2006 Boesser et al.
2006/0285638 A1 12/2006 Boese et al.
2006/0287595 A1 12/2006 Maschke
2006/0293597 A1 12/2006 Johnson et al.
2007/0015969 A1 1/2007 Feldman et al.
2007/0016029 A1 1/2007 Donaldson et al.
2007/0016034 A1 1/2007 Donaldson
2007/0016062 A1 1/2007 Park et al.
2007/0027390 A1 2/2007 Maschke et al.
2007/0036417 A1 2/2007 Argiro et al.
2007/0038061 A1 2/2007 Huennekens et al.
2007/0038121 A1 2/2007 Feldman et al.
2007/0038125 A1 2/2007 Kleen et al.
2007/0043292 A1 2/2007 Camus et al.
2007/0043597 A1 2/2007 Donaldson
2007/0049847 A1 3/2007 Osborne
2007/0060973 A1 3/2007 Ludvig et al.
2007/0065077 A1 3/2007 Childers et al.
2007/0066888 A1 3/2007 Maschke
2007/0066890 A1 3/2007 Maschke
2007/0066983 A1 3/2007 Maschke
2007/0084995 A1 4/2007 Newton et al.
2007/0100226 A1 5/2007 Yankelevitz et al.
2007/0135887 A1 6/2007 Maschke
2007/0142707 A1 6/2007 Wiklof et al.
2007/0156019 A1 7/2007 Larkin et al.
2007/0161893 A1 7/2007 Milner et al.
2007/0161896 A1 7/2007 Adachi et al.
2007/0161963 A1 7/2007 Smalling
2007/0162860 A1 7/2007 Muralidharan et al.
2007/0165141 A1 7/2007 Srinivas et al.
2007/0167710 A1 7/2007 Unal et al.
2007/0167804 A1 7/2007 Park et al.
2007/0191682 A1 8/2007 Rolland et al.
2007/0201736 A1 8/2007 Klingensmith et al.
2007/0206193 A1 9/2007 Pesach
2007/0208276 A1 9/2007 Kornkven Volk et al.
2007/0225220 A1 9/2007 Ming et al.
2007/0225590 A1 9/2007 Ramos
2007/0229801 A1 10/2007 Tearney et al.
2007/0232872 A1 10/2007 Prough et al.
2007/0232874 A1 10/2007 Ince
2007/0232890 A1 10/2007 Hirota
2007/0232891 A1 10/2007 Hirota
2007/0232892 A1 10/2007 Hirota
2007/0232893 A1 10/2007 Tanioka
2007/0232933 A1 10/2007 Gille et al.
2007/0238957 A1 10/2007 Yared
2007/0247033 A1 10/2007 Eidenschink et al.
2007/0250000 A1 10/2007 Magnin et al.
2007/0250036 A1 10/2007 Volk et al.
2007/0258094 A1 11/2007 Izatt et al.
2007/0260138 A1 11/2007 Feldman et al.
2007/0278389 A1 12/2007 Ajgaonkar et al.
2007/0287914 A1 12/2007 Cohen
2008/0002183 A1 1/2008 Yatagai et al.
2008/0013093 A1 1/2008 Izatt et al.
2008/0021275 A1 1/2008 Tearney et al.
2008/0027481 A1 1/2008 Gilson et al.
2008/0043024 A1 2/2008 Schiwietz et al.
2008/0045842 A1 2/2008 Furnish
2008/0051660 A1 2/2008 Kakadaris et al.
2008/0063304 A1 3/2008 Russak et al.
2008/0085041 A1 4/2008 Breeuwer
2008/0095465 A1 4/2008 Mullick et al.
2008/0095714 A1 4/2008 Castella et al.
2008/0097194 A1 4/2008 Milner
2008/0101667 A1 5/2008 Begelman et al.
2008/0108867 A1 5/2008 Zhou
2008/0114254 A1 5/2008 Matcovitch et al.
2008/0119739 A1 5/2008 Vardi et al.
2008/0124495 A1 5/2008 Horn et al.
2008/0125772 A1 5/2008 Stone et al.
2008/0139897 A1 6/2008 Ainsworth et al.

(56) References Cited

U.S. PATENT DOCUMENTS

2008/0143707 A1 6/2008 Mitchell
2008/0146941 A1 6/2008 Dala-Krishna
2008/0147111 A1 6/2008 Johnson et al.
2008/0154128 A1 6/2008 Milner
2008/0161696 A1 7/2008 Schmitt et al.
2008/0171944 A1 7/2008 Brenneman et al.
2008/0175465 A1 7/2008 Jiang et al.
2008/0177183 A1 7/2008 Courtney et al.
2008/0180683 A1 7/2008 Kemp
2008/0181477 A1 7/2008 Izatt et al.
2008/0187201 A1 8/2008 Liang et al.
2008/0228086 A1 9/2008 Ilegbusi et al.
2008/0247622 A1 10/2008 Aylward et al.
2008/0247716 A1 10/2008 Thomas et al.
2008/0262470 A1 10/2008 Lee et al.
2008/0262489 A1 10/2008 Steinke
2008/0269599 A1 10/2008 Csavoy et al.
2008/0281205 A1 11/2008 Naghavi et al.
2008/0281248 A1 11/2008 Angheloiu et al.
2008/0285043 A1 11/2008 Fercher et al.
2008/0287795 A1 11/2008 Klingensmith et al.
2008/0291463 A1 11/2008 Milner et al.
2008/0292173 A1 11/2008 Hsieh et al.
2008/0294034 A1 11/2008 Krueger et al.
2008/0298655 A1 12/2008 Edwards
2008/0306766 A1 12/2008 Ozeki et al.
2009/0009801 A1 1/2009 Tabuki
2009/0018393 A1 1/2009 Dick et al.
2009/0034813 A1 2/2009 Dikmen et al.
2009/0043191 A1 2/2009 Castella et al.
2009/0046295 A1 2/2009 Kemp et al.
2009/0052614 A1 2/2009 Hempel et al.
2009/0069843 A1 3/2009 Agnew
2009/0079993 A1 3/2009 Yatagai et al.
2009/0088650 A1 4/2009 Corl
2009/0093980 A1 4/2009 Kemp et al.
2009/0122320 A1 5/2009 Petersen et al.
2009/0138544 A1 5/2009 Wegenkittl et al.
2009/0149739 A9 6/2009 Maschke
2009/0156941 A1 6/2009 Moore
2009/0174886 A1 7/2009 Inoue
2009/0174931 A1 7/2009 Huber et al.
2009/0177090 A1 7/2009 Grunwald et al.
2009/0177183 A1 7/2009 Pinkernell et al.
2009/0195514 A1 8/2009 Glynn et al.
2009/0196470 A1 8/2009 Carl et al.
2009/0198125 A1 8/2009 Nakabayashi et al.
2009/0203991 A1 8/2009 Papaioannou et al.
2009/0264768 A1 10/2009 Courtney et al.
2009/0269014 A1 10/2009 Winberg et al.
2009/0270695 A1 10/2009 McEowen
2009/0284322 A1 11/2009 Harrison et al.
2009/0284332 A1 11/2009 Moore et al.
2009/0284749 A1 11/2009 Johnson et al.
2009/0290167 A1 11/2009 Flanders et al.
2009/0292048 A1 11/2009 Li et al.
2009/0299195 A1 12/2009 Muller et al.
2009/0299284 A1 12/2009 Holman et al.
2009/0318951 A1 12/2009 Kashkarov et al.
2009/0326634 A1 12/2009 Vardi
2010/0007669 A1 1/2010 Bethune et al.
2010/0030042 A1 2/2010 Denninghoff et al.
2010/0061611 A1 3/2010 Xu et al.
2010/0063400 A1 3/2010 Hall et al.
2010/0087732 A1 4/2010 Eberle et al.
2010/0094125 A1 4/2010 Younge et al.
2010/0094127 A1 4/2010 Xu
2010/0094135 A1 4/2010 Fang-Yen et al.
2010/0094143 A1 4/2010 Mahapatra et al.
2010/0113919 A1 5/2010 Maschke
2010/0125238 A1 5/2010 Lye et al.
2010/0125268 A1 5/2010 Gustus et al.
2010/0125648 A1 5/2010 Zaharia et al.
2010/0128348 A1 5/2010 Taverner
2010/0152717 A1 6/2010 Keeler
2010/0160788 A1 6/2010 Davies et al.
2010/0161023 A1 6/2010 Cohen et al.
2010/0168714 A1 7/2010 Burke et al.
2010/0179421 A1 7/2010 Tupin
2010/0179426 A1 7/2010 Davies et al.
2010/0220334 A1 9/2010 Condit et al.
2010/0226607 A1 9/2010 Zhang et al.
2010/0234736 A1 9/2010 Corl
2010/0249601 A1 9/2010 Courtney
2010/0256616 A1 10/2010 Katoh et al.
2010/0272432 A1 10/2010 Johnson
2010/0280315 A1* 11/2010 Pan .............................. 600/109
2010/0284590 A1 11/2010 Peng et al.
2010/0290693 A1 11/2010 Cohen et al.
2010/0331950 A1 12/2010 Strommer
2011/0010925 A1 1/2011 Nix et al.
2011/0021926 A1 1/2011 Spencer et al.
2011/0025853 A1 2/2011 Richardson
2011/0026797 A1 2/2011 Declerck et al.
2011/0032533 A1 2/2011 Izatt et al.
2011/0034801 A1 2/2011 Baumgart
2011/0044546 A1 2/2011 Pan et al.
2011/0066073 A1 3/2011 Kuiper et al.
2011/0071401 A1 3/2011 Hastings et al.
2011/0072405 A1 3/2011 Chen et al.
2011/0077528 A1 3/2011 Kemp et al.
2011/0080591 A1 4/2011 Johnson et al.
2011/0087104 A1 4/2011 Moore et al.
2011/0137140 A1 6/2011 Tearney et al.
2011/0144502 A1 6/2011 Zhou et al.
2011/0152771 A1 6/2011 Milner et al.
2011/0157597 A1 6/2011 Lu et al.
2011/0160586 A1 6/2011 Li et al.
2011/0178413 A1 7/2011 Schmitt et al.
2011/0190586 A1 8/2011 Kemp
2011/0216378 A1 9/2011 Poon et al.
2011/0220985 A1 9/2011 Son et al.
2011/0238061 A1 9/2011 van der Weide et al.
2011/0238083 A1 9/2011 Moll et al.
2011/0245669 A1 10/2011 Zhang
2011/0249094 A1 10/2011 Wang et al.
2011/0257545 A1 10/2011 Suri
2011/0264125 A1 10/2011 Wilson et al.
2011/0274329 A1 11/2011 Mathew et al.
2011/0282334 A1 11/2011 Groenhoff
2011/0301684 A1 12/2011 Fischell et al.
2011/0306995 A1 12/2011 Moberg
2011/0319752 A1 12/2011 Steinberg
2012/0004529 A1 1/2012 Tolkowsky et al.
2012/0004668 A1 1/2012 Wallace et al.
2012/0013914 A1 1/2012 Kemp et al.
2012/0016344 A1 1/2012 Kusakabe
2012/0016395 A1 1/2012 Olson
2012/0022360 A1 1/2012 Kemp
2012/0026503 A1 2/2012 Lewandowski et al.
2012/0029007 A1 2/2012 Graham et al.
2012/0059253 A1 3/2012 Wang et al.
2012/0059368 A1 3/2012 Takaoka et al.
2012/0062843 A1 3/2012 Ferguson et al.
2012/0065481 A1 3/2012 Hunter et al.
2012/0071823 A1 3/2012 Chen
2012/0071838 A1 3/2012 Fojtik
2012/0075638 A1 3/2012 Rollins et al.
2012/0083696 A1 4/2012 Kitamura
2012/0095340 A1 4/2012 Smith
2012/0095372 A1 4/2012 Sverdlik et al.
2012/0108943 A1 5/2012 Bates et al.
2012/0113108 A1 5/2012 Dala-Krishna
2012/0116353 A1 5/2012 Arnold et al.
2012/0130243 A1 5/2012 Balocco et al.
2012/0130247 A1 5/2012 Waters et al.
2012/0136259 A1 5/2012 Milner et al.
2012/0136427 A1 5/2012 Palmaz et al.
2012/0137075 A1 5/2012 Vorbach
2012/0155734 A1 6/2012 Barratt et al.
2012/0158101 A1 6/2012 Stone et al.
2012/0162660 A1 6/2012 Kemp
2012/0165661 A1 6/2012 Kemp et al.
2012/0170848 A1 7/2012 Kemp et al.

(56) References Cited

U.S. PATENT DOCUMENTS

| | | | |
|---|---|---|---|
| 2012/0172698 | A1 | 7/2012 | Teo et al. |
| 2012/0176607 | A1 | 7/2012 | Ott |
| 2012/0184853 | A1 | 7/2012 | Waters |
| 2012/0184859 | A1 | 7/2012 | Shah et al. |
| 2012/0184977 | A1 | 7/2012 | Wolf |
| 2012/0215094 | A1 | 8/2012 | Rahimian et al. |
| 2012/0220836 | A1 | 8/2012 | Alpert et al. |
| 2012/0220851 | A1 | 8/2012 | Razansky et al. |
| 2012/0220865 | A1 | 8/2012 | Brown et al. |
| 2012/0220874 | A1 | 8/2012 | Hancock et al. |
| 2012/0220883 | A1 | 8/2012 | Manstrom et al. |
| 2012/0224751 | A1 | 9/2012 | Kemp et al. |
| 2012/0226153 | A1 | 9/2012 | Brown et al. |
| 2012/0230565 | A1 | 9/2012 | Steinberg et al. |
| 2012/0232400 | A1 | 9/2012 | Dickinson et al. |
| 2012/0238869 | A1 | 9/2012 | Schmitt et al. |
| 2012/0238956 | A1 | 9/2012 | Yamada et al. |
| 2012/0244043 | A1 | 9/2012 | Leblanc et al. |
| 2012/0250028 | A1 | 10/2012 | Schmitt et al. |
| 2012/0253186 | A1 | 10/2012 | Simpson et al. |
| 2012/0253192 | A1 | 10/2012 | Cressman |
| 2012/0253276 | A1 | 10/2012 | Govari et al. |
| 2012/0257210 | A1 | 10/2012 | Whitney et al. |
| 2012/0262720 | A1 | 10/2012 | Brown et al. |
| 2012/0265077 | A1 | 10/2012 | Gille et al. |
| 2012/0265268 | A1 | 10/2012 | Blum et al. |
| 2012/0265296 | A1 | 10/2012 | McNamara et al. |
| 2012/0271170 | A1 | 10/2012 | Emelianov et al. |
| 2012/0271175 | A1 | 10/2012 | Moore et al. |
| 2012/0271339 | A1 | 10/2012 | O'Beirne et al. |
| 2012/0274338 | A1 | 11/2012 | Baks et al. |
| 2012/0276390 | A1 | 11/2012 | Ji et al. |
| 2012/0277722 | A1 | 11/2012 | Gerber et al. |
| 2012/0279764 | A1 | 11/2012 | Jiang et al. |
| 2012/0283758 | A1 | 11/2012 | Miller et al. |
| 2012/0289987 | A1 | 11/2012 | Wilson et al. |
| 2012/0299439 | A1 | 11/2012 | Huang |
| 2012/0310081 | A1 | 12/2012 | Adler et al. |
| 2012/0310332 | A1 | 12/2012 | Murray et al. |
| 2012/0319535 | A1 | 12/2012 | Dausch |
| 2012/0323075 | A1 | 12/2012 | Younge et al. |
| 2012/0323127 | A1 | 12/2012 | Boyden et al. |
| 2012/0330141 | A1 | 12/2012 | Brown et al. |
| 2013/0015975 | A1 | 1/2013 | Huennekens et al. |
| 2013/0023762 | A1 | 1/2013 | Huennekens et al. |
| 2013/0023763 | A1 | 1/2013 | Huennekens et al. |
| 2013/0026655 | A1 | 1/2013 | Lee et al. |
| 2013/0030295 | A1 | 1/2013 | Huennekens et al. |
| 2013/0030303 | A1 | 1/2013 | Ahmed et al. |
| 2013/0030410 | A1 | 1/2013 | Drasler et al. |
| 2013/0053949 | A1 | 2/2013 | Pintor et al. |
| 2013/0085378 | A1* | 4/2013 | Wedan et al. ................. 600/417 |
| 2013/0109958 | A1 | 5/2013 | Baumgart et al. |
| 2013/0109959 | A1 | 5/2013 | Baumgart et al. |
| 2013/0137980 | A1 | 5/2013 | Waters et al. |
| 2013/0150716 | A1 | 6/2013 | Stigall et al. |
| 2013/0158594 | A1 | 6/2013 | Carrison et al. |
| 2013/0218201 | A1 | 8/2013 | Obermiller et al. |
| 2013/0218267 | A1 | 8/2013 | Braido et al. |
| 2013/0223789 | A1 | 8/2013 | Lee et al. |
| 2013/0223798 | A1 | 8/2013 | Jenner et al. |
| 2013/0296704 | A1 | 11/2013 | Magnin et al. |
| 2013/0303907 | A1 | 11/2013 | Corl |
| 2013/0303920 | A1 | 11/2013 | Corl |
| 2013/0310698 | A1 | 11/2013 | Judell et al. |
| 2013/0331820 | A1 | 12/2013 | Itou et al. |
| 2013/0338766 | A1 | 12/2013 | Hastings et al. |
| 2013/0339958 | A1 | 12/2013 | Droste et al. |
| 2014/0039294 | A1 | 2/2014 | Jiang |
| 2014/0180067 | A1 | 6/2014 | Stigall et al. |
| 2014/0180128 | A1 | 6/2014 | Corl |
| 2014/0200438 | A1 | 7/2014 | Millett et al. |

FOREIGN PATENT DOCUMENTS

| | | | |
|---|---|---|---|
| EP | 2438877 | A2 | 4/2012 |
| GB | 2280261 | A | 1/1995 |
| JP | 2000-262461 | A | 9/2000 |
| JP | 2000-292260 | A | 10/2000 |
| JP | 2001-125009 | A | 5/2001 |
| JP | 2001-272331 | A | 10/2001 |
| JP | 2002-374034 | A | 12/2002 |
| JP | 2003-143783 | A | 5/2003 |
| JP | 2003-172690 | A | 6/2003 |
| JP | 2003-256876 | A | 9/2003 |
| JP | 2003-287534 | A | 10/2003 |
| JP | 2005-274380 | A | 10/2005 |
| JP | 2006-184284 | A | 7/2006 |
| JP | 2006-266797 | A | 10/2006 |
| JP | 2006-313158 | A | 11/2006 |
| JP | 2007-024677 | A | 2/2007 |
| JP | 2009-233001 | A | 10/2009 |
| JP | 2011-56786 | A | 3/2011 |
| WO | 91/01156 | A1 | 2/1991 |
| WO | 92/16865 | A1 | 10/1992 |
| WO | 93/06213 | A1 | 4/1993 |
| WO | 93/08829 | A1 | 5/1993 |
| WO | 98/38907 | A1 | 9/1998 |
| WO | 98/57583 | A1 | 12/1998 |
| WO | 00/11511 | A1 | 3/2000 |
| WO | 00/44296 | A1 | 8/2000 |
| WO | 01/11409 | A2 | 2/2001 |
| WO | 03/062802 | A2 | 7/2003 |
| WO | 03/073950 | A1 | 9/2003 |
| WO | 2004/010856 | A1 | 2/2004 |
| WO | 2004/023992 | A1 | 3/2004 |
| WO | 2004/096049 | A2 | 11/2004 |
| WO | 2005/047813 | A1 | 5/2005 |
| WO | 2005/106695 | A2 | 11/2005 |
| WO | 2006/029634 | A2 | 3/2006 |
| WO | 2006/037132 | A1 | 4/2006 |
| WO | 2006/039091 | A2 | 4/2006 |
| WO | 2006/061829 | A1 | 6/2006 |
| WO | 2006/068875 | A2 | 6/2006 |
| WO | 2006/111704 | A1 | 10/2006 |
| WO | 2006/119416 | A2 | 11/2006 |
| WO | 2006/121851 | A2 | 11/2006 |
| WO | 2006/130802 | A2 | 12/2006 |
| WO | 2007/002685 | A2 | 1/2007 |
| WO | 2007/025230 | A2 | 3/2007 |
| WO | 2007/045690 | A1 | 4/2007 |
| WO | 2007/058895 | A2 | 5/2007 |
| WO | 2007/067323 | A2 | 6/2007 |
| WO | 2007/084995 | A2 | 7/2007 |
| WO | 2008/058084 | A2 | 5/2008 |
| WO | 2008/069991 | A1 | 6/2008 |
| WO | 2008/107905 | A2 | 9/2008 |
| WO | 2009/009799 | A1 | 1/2009 |
| WO | 2009/009801 | A1 | 1/2009 |
| WO | 2009/046431 | A1 | 4/2009 |
| WO | 2009/121067 | A1 | 10/2009 |
| WO | 2009/137704 | A1 | 11/2009 |
| WO | 2011/006886 | A2 | 1/2011 |
| WO | 2011/038048 | A1 | 3/2011 |
| WO | 2011/081688 | A1 | 7/2011 |
| WO | 2012/003369 | A2 | 1/2012 |
| WO | 2012/061935 | A1 | 5/2012 |
| WO | 2012/071388 | A2 | 5/2012 |
| WO | 2012/087818 | A1 | 6/2012 |
| WO | 2012/098194 | A1 | 7/2012 |
| WO | 2012/109676 | A1 | 8/2012 |
| WO | 2012/130289 | A1 | 10/2012 |
| WO | 2012/154767 | A2 | 11/2012 |
| WO | 2012/155040 | A1 | 11/2012 |
| WO | 2013/033414 | A1 | 3/2013 |
| WO | 2013/033415 | A2 | 3/2013 |
| WO | 2013/033418 | A1 | 3/2013 |
| WO | 2013/033489 | A1 | 3/2013 |
| WO | 2013/033490 | A1 | 3/2013 |
| WO | 2013/033592 | A1 | 3/2013 |
| WO | 2013/126390 | A1 | 8/2013 |
| WO | 2014/109879 | A1 | 7/2014 |

(56) References Cited

FOREIGN PATENT DOCUMENTS

OTHER PUBLICATIONS

Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60 (9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18 (17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radiofrequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27,2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12 (24):6033-6039.
Zitova et al., 2003, Image registration methods: A survey. Image and Vision Computing, 21(11):977-1000.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.

(56) References Cited

OTHER PUBLICATIONS

Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61 (1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (Miller) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion mailed Mar. 11, 2014, for International Patent Application No. PCT/US13/75675, filed Dec. 17, 2013 (7 pages).
International Search Report and Written Opinion mailed Mar. 19, 2014, for International Patent Application No. PCT/US13/075353, filed Dec. 16, 2013 (8 pages).
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The Miller banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.

(56) References Cited

OTHER PUBLICATIONS

Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87 (suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26 (1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4)1 547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
International Search Report and Written Opinion mailed Nov. 2, 2012, for International Patent Application No. PCT/US12/53168, filed Aug. 30, 2013 (8 pages).
International Search Report and Written Opinion mailed on Apr. 14, 2014, for International Patent Application No. PCT/US2013/076148, filed Dec. 18, 2013 (8 pages).
International Search Report and Written Opinion mailed on Apr. 21, 2014, for International Patent Application No. PCT/US2013/076015, filed Dec. 18, 2013 (7 pages).
International Search Report and Written Opinion mailed on Apr. 23, 2014, for International Patent Application No. PCT/US2013/075328, filed Dec. 16, 2013 (8 pages).
International Search Report and Written Opinion mailed on Apr. 29, 2014, for International Patent Application No. PCT/US13/76093, filed Dec. 18, 2013 (6 pages).
International Search Report and Written Opinion mailed on Apr. 9, 2014, for International Patent Application No. PCT/US13/75089, filed Dec. 13, 2013 (7 pages).
International Search Report and Written Opinion mailed on Feb. 21, 2014, for International Patent Application No. PCT/US13/76053, filed Dec. 18, 2013 (9 pages).
International Search Report and Written Opinion mailed on Feb. 21, 2014, for International Patent Application No. PCT/US2013/076965, filed Dec. 20, 2013 (6 pages).
International Search Report and Written Opinion mailed on Feb. 27, 2014, for International Patent Application No. PCT/US13/75416, filed Dec. 16, 2013 (7 pages).
International Search Report and Written Opinion mailed on Feb. 28, 2014, for International Patent Application No. PCT/US13/75653, filed Dec. 17, 2013 (7 pages).
International Search Report and Written Opinion mailed on Feb. 28, 2014, for International Patent Application No. PCT/US13/75990, filed Dec. 18, 2013 (7 pages).
International Search Report and Written Opinion mailed on Jan. 16, 2009, for International Patent Application No. PCT/US08/78963 filed on Oct. 6, 2008 (7 Pages).
International Search Report and Written Opinion mailed on Jul. 30, 2014, for International Patent Application No. PCT/US14/21659, filed Mar. 7, 2014 (15 pages).
International Search Report and Written Opinion mailed on Mar. 10, 2014, for International Patent Application No. PCT/US2013/076212, filed Dec. 18, 2013 (8 pages).
International Search Report and Written Opinion mailed on Mar. 11, 2014, for International Patent Application No. PCT/US13/76173, filed Dec. 16, 2013 (9 pages).
International Search Report and Written Opinion mailed on Mar. 11, 2014, for International Patent Application No. PCT/US13/76449, filed Dec. 19, 2013 (9 pages).

(56) References Cited

OTHER PUBLICATIONS

International Search Report and Written Opinion mailed on Mar. 18, 2014, for International Patent Application No. PCT/US2013/076502, filed Dec. 19, 2013 (7 pages).
International Search Report and Written Opinion mailed on Mar. 18, 2014, for International Patent Application No. PCT/US2013/076788, filed Dec. 20, 2013 (7 pages).
International Search Report and Written Opinion mailed on Mar. 19, 2014, for International Patent Application No. PCT/US13/75349, filed Dec. 16, 2013 (10 pages).
International Search Report and Written Opinion mailed on Mar. 19, 2014, for International Patent Application No. PCT/US2013/076587, filed Dec. 19, 2013 (10 pages).
International Search Report and Written Opinion mailed on Mar. 19, 2014, for International Patent Application No. PCT/US2013/076909, filed Dec. 20, 2013 (7 pages).
International Search Report and Written Opinion mailed on Mar. 7, 2014, for International Patent Application No. PCT/US2013/076304, filed Dec. 18, 2013 (9 pages).
International Search Report and Written Opinion mailed on Mar. 7, 2014, for International Patent Application No. PCT/US2013/076480, filed Dec. 19, 2013 (8 pages).
International Search Report and Written Opinion mailed on Mar. 7, 2014, for International Patent Application No. PCT/US2013/076512, filed Dec. 19, 2013 (8 pages).
International Search Report and Written Opinion mailed on Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barret's Esophagus, Endoscopy, 32(12):921-930.

* cited by examiner

SYSTEM AND METHOD FOR OCT DEPTH CALIBRATION

FIELD OF THE INVENTION

This application claims the benefit of, and priority to, U.S. Provisional Patent Application No. 61/778,761, filed Mar. 13, 2013, which is incorporated by reference.

FIELD OF THE INVENTION

The invention relates to methods for calibrating optical coherence tomography images.

BACKGROUND

Intravascular optical coherence tomography (OCT) systems operate via a rotating catheter that is introduced into a patient's blood vessels to image the vessel walls to detect atherosclerotic plaque and other life-threatening conditions. The catheter takes a picture by shooting beams of light as it rotates and translates within the vessel and detecting light that is reflected back. The light is detected in the form of a series of lines arranged in a helix. A computer processor can digitize the information and arrange it for presentation on a screen.

One problem in OCT is calibration. The lines are treated as if they originate at the center of the fiber optical catheter, but this is based on assumptions about the path length of light through the catheter. The catheter is, in-fact, subject to stresses that can distort the path length during imaging. Thus, if the catheter stretches by a millimeter during imaging, the radius to a point on each line is artificially shrunken by a millimeter. If a diameter is measured on that image, the diameter will be wrong by two millimeters.

Unfortunately, the fiber optical catheter is within a patient during imaging and the imaging proceeds rapidly, so it is not realistic for an attendant to stand by and measure stretching or distortion of the catheter. Since one measure of the severity of atherosclerosis is cross-sectional area of space within a blood vessel, path length changes in OCT imaging hardware interfere with accurately evaluating the severity of a patient's condition.

SUMMARY

The invention provides systems and methods for calibrating OCT images by detecting a feature within the image, where a position of the feature within the actual patient is known. For example, a surface of an imaging catheter can be detected automatically within the OCT image. If the diameter of the catheter is known a priori, the detected location can be compared to the expected location to determine a path length distortion. The image can be transformed to correct for the path length distortion, thereby repositioning all of the pixels into locations that accurately depict the bodily tissue. This provides a calibrated image in which apparent dimensions in the image display (e.g., as seen on a computer monitor) can be used to faithfully determine actual dimensions of medically significant features within a patient's body. Thus OCT imaging can be used to evaluate the severity of atherosclerosis by, for example, revealing the actual space through a blood vessel through which blood may flow.

In certain aspects, the invention provides a method of calibrating an imaging system by obtaining an image that includes a target and a reference item, detecting a location of the reference item within the image, determining a y-value of the location, comparing the determined y-value to a stored reference y-value, calculating a calibration value based on the comparison, and providing a calibrated image by shifting pixels in a y-direction according to the calibration value. The imaging system may be an optical coherence tomography system. The reference item may be an image of a catheter sheath. The detecting step may include a morphological image processing operation. The method may include digitally transforming image data to provide the calibrated image. Detecting the location may include peak searching, correlation, thresholding, or performing a pattern recognition algorithm. The method may involve obtaining an a priori range over which a path length displacement may occur. Determining the y-value may include averaging across the image. Calculating the calibration value may include taking a difference between the determined y-value and the stored reference y-value.

In some embodiments, a feature is also removed (cropped) from the image. For example, the detected reference item may be removed from the image. Removing may be by cropping out the feature across its extent in the y direction at all x positions. Cropping or removing a feature may include calculating an average value of pixels proximal to the cropped region and inserting the average values to replace the cropped pixels.

In certain embodiments, any or all of the foregoing steps are performed using a computer system comprising a tangible, non-transitory memory coupled to a processor. In related aspects, the invention provides a system for providing a calibrated image, in which the system includes a memory coupled to a processor, the system being operable to perform any of the foregoing steps.

DETAILED DESCRIPTION

Figure 1:
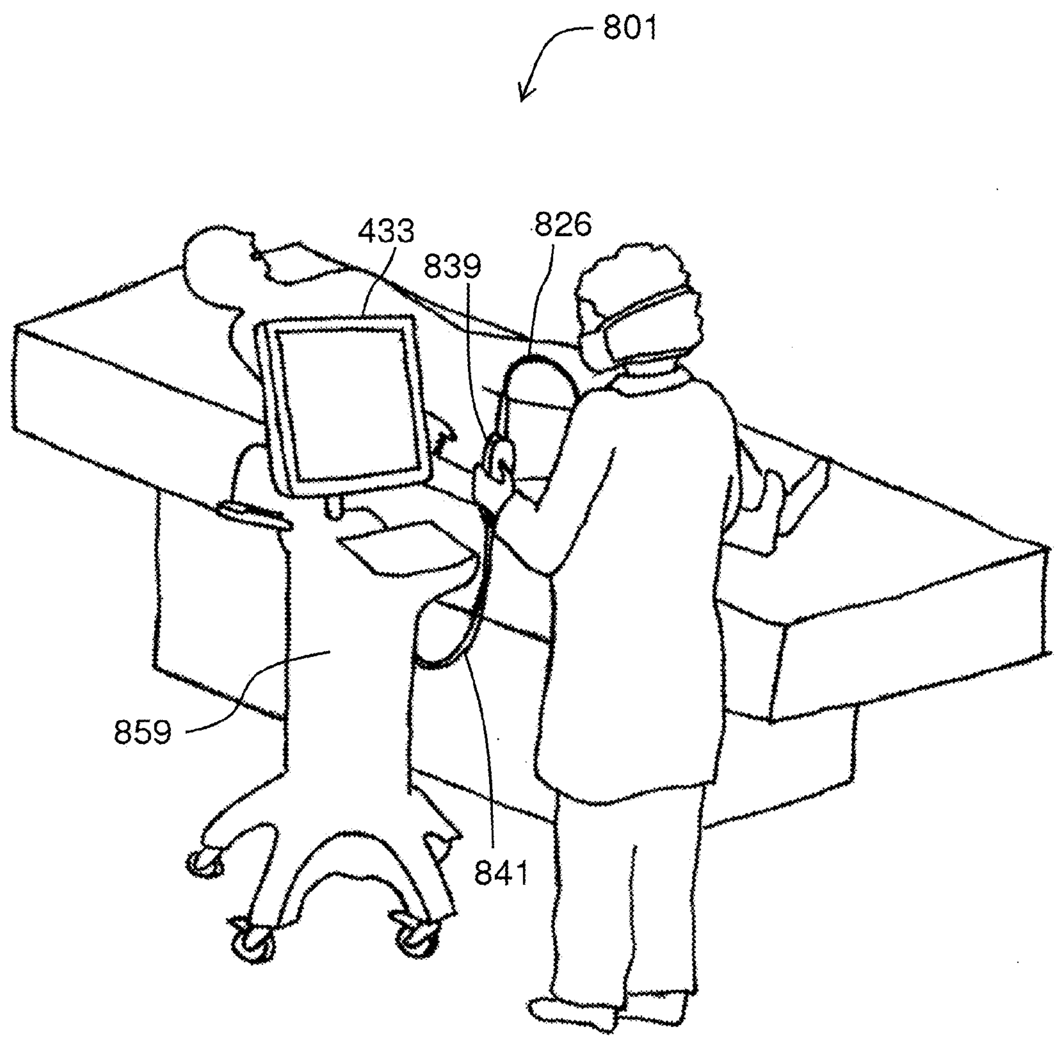
FIG. 1 shows use of an imaging system according to certain embodiments.

The invention provides systems and methods for calibrating an imaging system. Systems and methods of the invention have application in imaging systems that require calibration to provide a scale. Exemplary systems include imaging and sensing systems based on principles of rotational imaging. In some embodiments, systems and applications contemplated for use with the invention include optical coherence tomography (OCT).

In OCT systems, a light source is used to provide a beam of coherent light. The light source can include an optical gain medium (e.g., laser or optical amplifier) to produce coherent light by stimulated emission. In some embodiments, the gain medium is provided by a semiconductor optical amplifier. A light source may further include other components, such as a tunable filter that allows a user to select a wavelength of light to be amplified. Wavelengths commonly used in medical applications include near-infrared light, for example between about 800 nm and about 1700 nm.

Generally, there are two types of OCT systems, common beam path systems and differential beam path systems, that differ from each other based upon the optical layout of the systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are further described for example in U.S. Pat. Nos. 7,999,938; 7,995,210; and 7,787,127 the contents of each of which are incorporated by reference herein in their entirety.

In a differential beam path system, the coherent light from the light source is input into an interferometer and split into a reference path and a sample path. The sample path is directed to the target and used to image the target. Reflections from the sample path are joined with the reference path and the combination of the reference-path light and the sample-path light produces interference patterns in the resulting light. The light, and thus the patterns, are converted to electric signals, which are then analyzed to produce depth-resolved images of the target tissue on a micron scale. Exemplary differential beam path interferometers are Mach-Zehnder interferometers and Michelson interferometers. Differential beam path interferometers are further described for example in U.S. Pat. Nos. 7,783,337; 6,134,003; and 6,421,164, the contents of each of which are incorporated by reference herein in its entirety.

Commercially available OCT systems are employed in diverse applications, including art conservation and diagnostic medicine, notably in ophthalmology where OCT can be used to obtain detailed images from within the retina. The detailed images of the retina allow one to identify diseases and trauma of the eye. Other applications of imaging systems of the invention include, for example, dermatology (e.g., to image subsurface structural and blood flow formations), dentistry (to image teeth and gum line), gastroenterology (e.g., to image the gastrointestinal tract to detect polyps and inflammation), and cancer diagnostics (for example, to discriminate between malignant and normal tissue).

In certain embodiments, systems and methods of the invention image within a lumen of tissue. Various lumen of biological structures may be imaged including, for example, blood vessels, including, but not limited, to vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus and fallopian tubes, structures of the urinary tract including urinary collecting ducts, renal tubules, ureter, and bladder, and structures of the head and neck and pulmonary system including sinuses, parotid, trachea, bronchi, and lungs. Systems and methods of the invention have particular applicability in imaging veins and arteries such as, for example, the arteries of the heart. Since an OCT system can be calibrated to provide scale information, intravascular OCT imaging of the coronary arteries can reveal plaque build-up over time, change in dimensions of features, and progress of thrombotic elements. The accumulation of plaque within the artery wall over decades is the setup for vulnerable plaque which, in turn, leads to heart attack and stenosis (narrowing) of the artery. OCT images, if scaled or calibrated, are useful in determining both plaque volume within the wall of the artery and/or the degree of stenosis of the artery lumen. Intravascular OCT can also be used to assess the effects of treatments of stenosis such as with hydraulic angioplasty expansion of the artery, with or without stents, and the results of medical therapy over time.

FIG. 1 depicts the use of an exemplary intravascular OCT system 801. A physician controls an imaging catheter 826 through use of a handheld patient interface module (PIM) 839 to collect image data from a patient. Image data collected through catheter 826 is transmitted by PIM cable 841 to an imaging engine 859, which can be, for example, housed within a bedside unit or in a nearby computer installation or in a server rack coupled via networking technologies. As shown in FIG. 1, an OCT system can further include a workstation 433 (e.g., a monitor, keyboard, and mouse).

Figure 2:
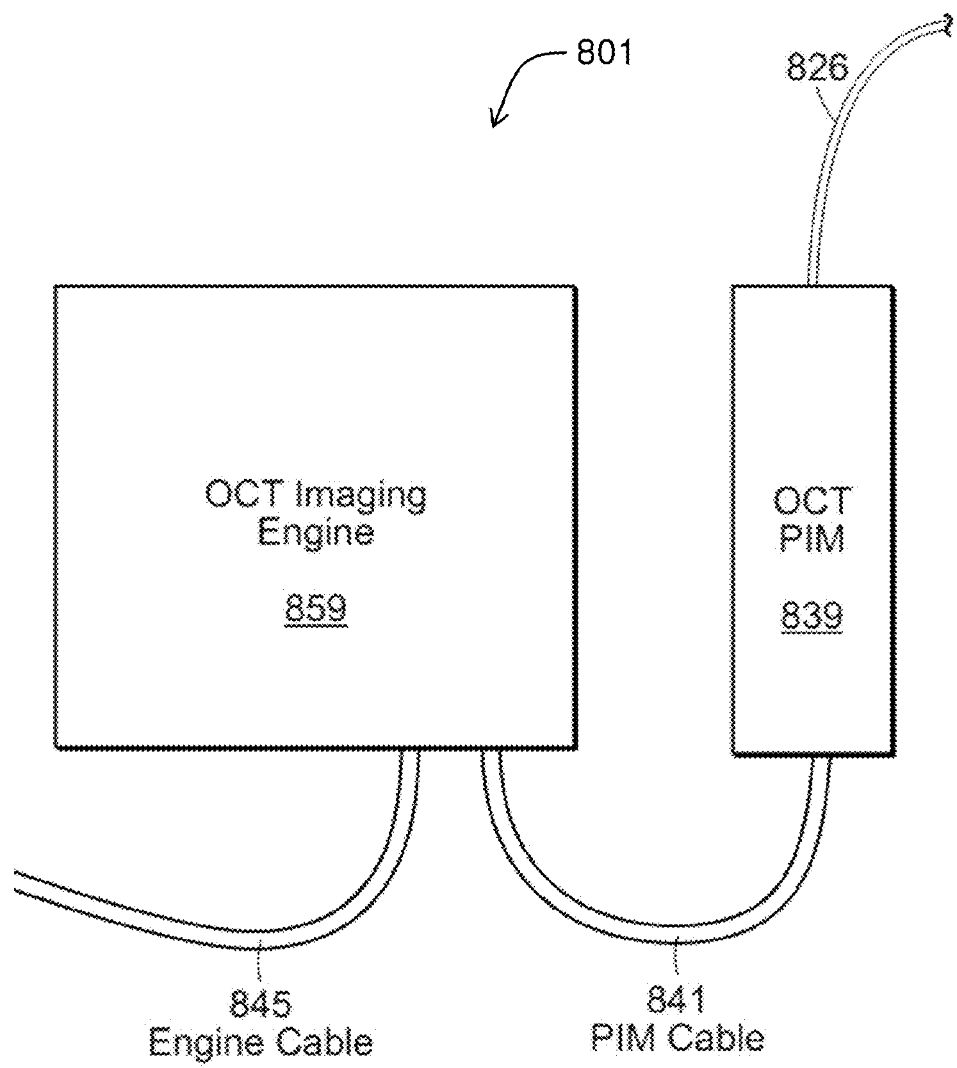
FIG. 2 is a diagram of components of an OCT system.

FIG. 2 gives a block diagram of components of OCT system 801. Imaging engine 859 is coupled to PIM 839 via PIM cable 841. Imaging catheter 826 extends from PIM 839 to the site of imaging. Engine cable 845 connects imaging engine 859 to host workstation 433. OCT is discussed in U.S. Pat. No. 8,108,030; U.S. Pub. 2011/0152771; U.S. Pub. 2010/0220334; U.S. Pub. 2009/0043191; U.S. Pub. 2008/0291463; and U.S. Pub. 2008/0180683, the contents of each of which are incorporated by reference in their entirety for all purposes. In certain embodiments, systems and methods of the invention include processing hardware configured to interact with more than one different three dimensional imaging system so that the tissue imaging devices and methods described here in can be alternatively used with OCT, IVUS, or other hardware.

As shown in FIG. 1, an operator controls imaging catheter 826 via handheld PIM 839. PIM 839 may include controls such as knobs or buttons to start or stop operation, set or vary speed or displacement, or otherwise control the imaging operation. PIM 839 further includes hardware for operating the imaging catheter.

Figure 3:
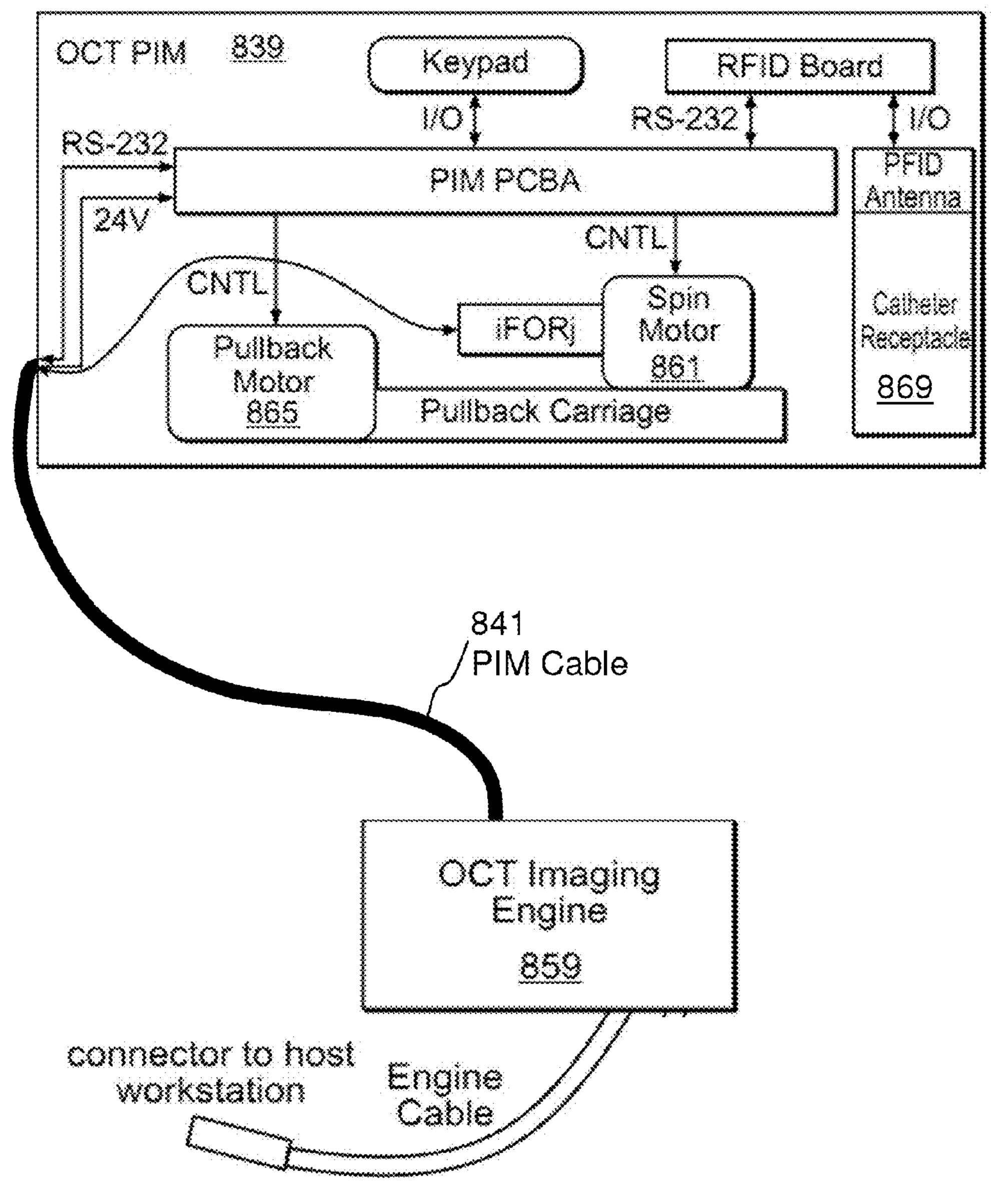
FIG. 3 diagrams components within a patient interface module (PIM).

FIG. 3 shows components of PIM 839. Catheter 826 is mounted to PIM 839 via a catheter receptacle 869. Spin motor 861 is provided to rotate catheter 826 and pullback motor 865 is provided to drive lateral translation of catheter 826. Also depicted is a keypad for input/output, a fiber-optic rotary joint (iFORj), a printed circuit board assembly (PCBA), and optional RFID components.

Figure 4:
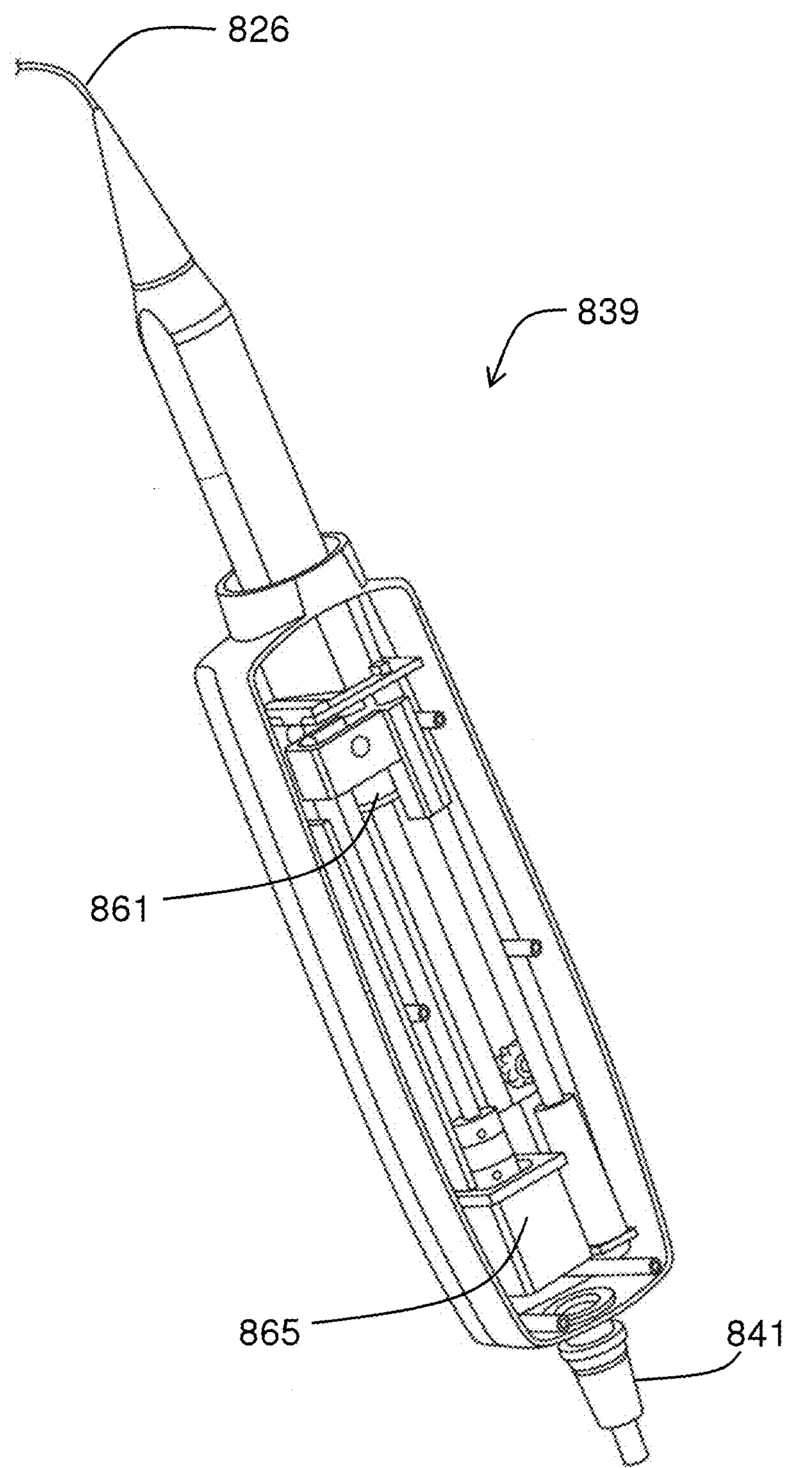
FIG. 4 shows the structure of a PIM according to certain embodiments.

FIG. 4 gives a perspective view of PIM 839 with a keypad cover removed. Spin motor 861 is provided to rotate catheter 826 and pullback motor 865 causes lateral translation. Optical signals, electrical signals, or both arrive at PIM 839 via PIM cable 841. PIM cable 841 extends to imaging engine 859 as shown in FIG. 2.

Figure 5:
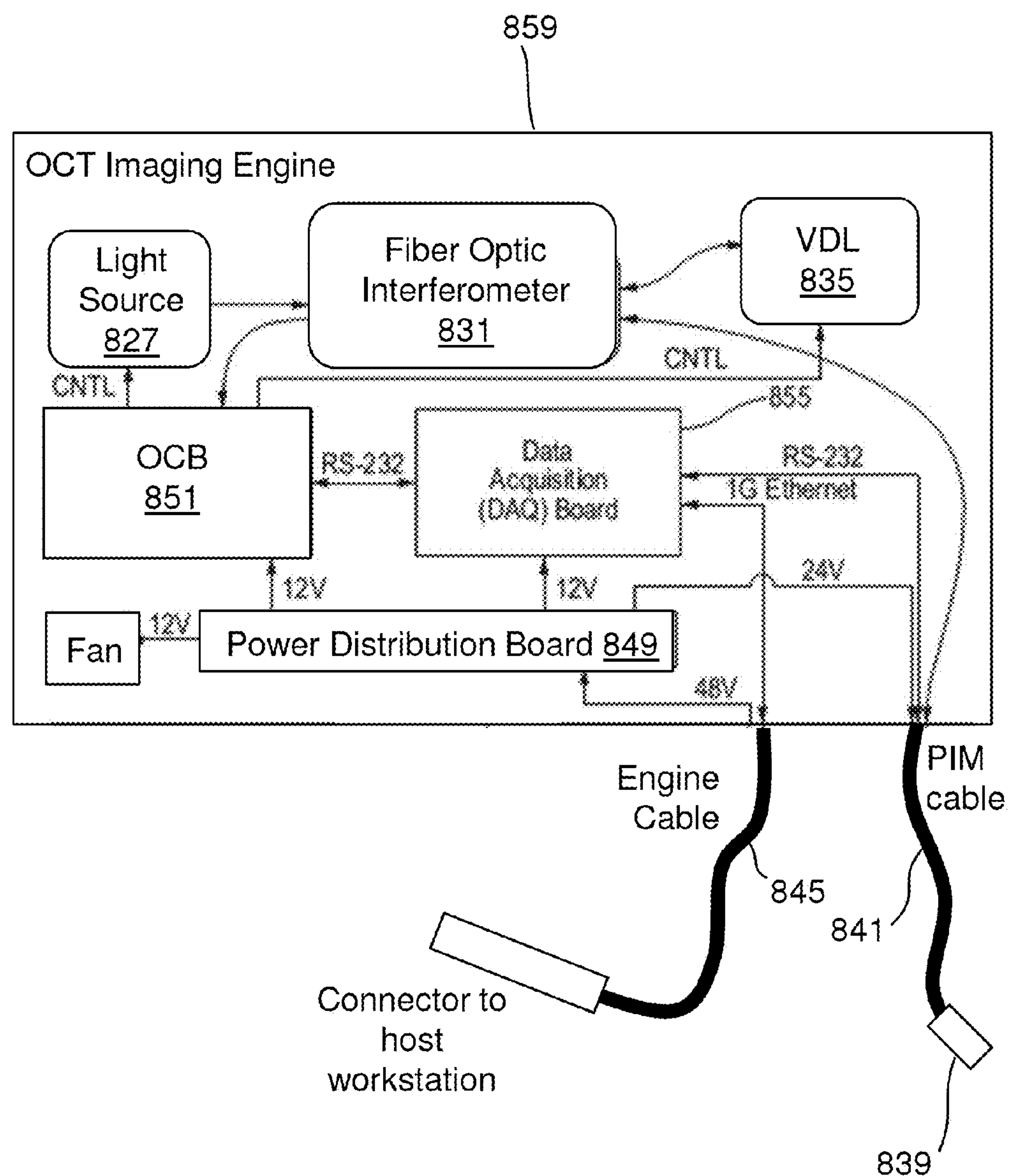
FIG. 5 is a diagram of components in an imaging engine.

FIG. 5 shows components of imaging engine 859. As shown in FIG. 5, the imaging engine 859 (e.g., a bedside unit) houses a power distribution board 849, light source 827, interferometer 831, and variable delay line 835 as well as a data acquisition (DAQ) board 855 and optical controller board (OCB) 851.

Light source 827, as discussed above, may use a laser or an optical amplifier as a source of coherent light. Coherent light is transmitted to interferometer 831.

Figure 6:
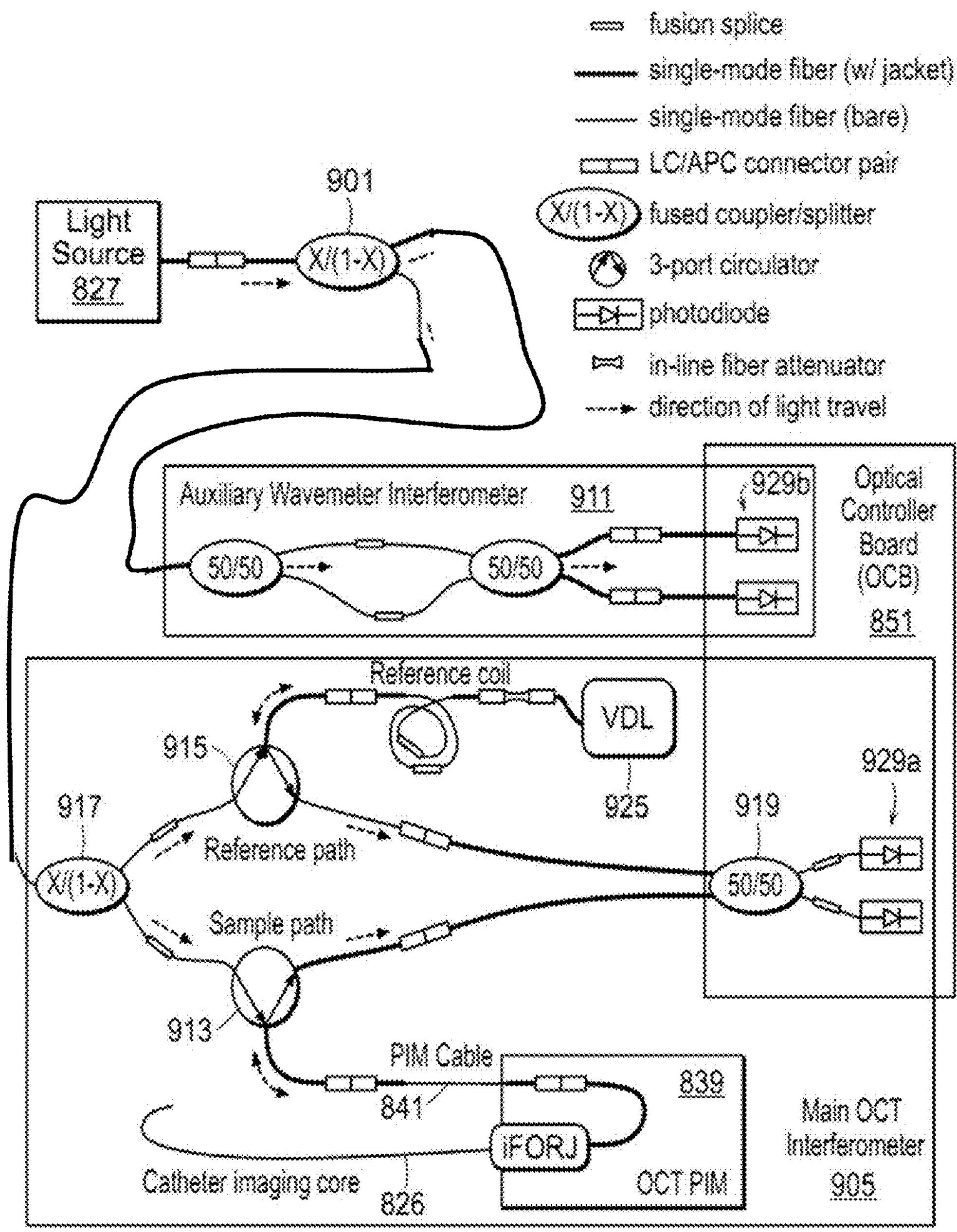
FIG. 6 is a diagram of an interferometer for use with systems of certain embodiments.

FIG. 6 shows a path of light through interferometer 831 during OCT imaging. Coherent light for image capture originates within the light source 827. This light is split between an OCT interferometer 905 and an auxiliary, or "clock", interferometer 911. Light directed to the OCT interferometer is further split by splitter 917 and recombined by splitter 919 with an asymmetric split ratio. The majority of the light is guided into the sample path 913 and the remainder into a reference path 915. The sample path includes optical fibers running through the PIM 839 and the imaging catheter 826 and terminating at the distal end of the imaging catheter where the image is captured.

An image is captured by introducing imaging catheter 826 into a target within a patient, such as a lumen of a blood vessel. This can be accomplished by using standard interventional techniques and tools such as a guide wire, guide catheter, or angiography system. Suitable imaging catheters and their use are discussed in U.S. Pat. No. 8,116,605 and U.S. Pat. No. 7,711,413, the contents of which are incorporated by reference in their entirety for all purposes.

Figure 7:
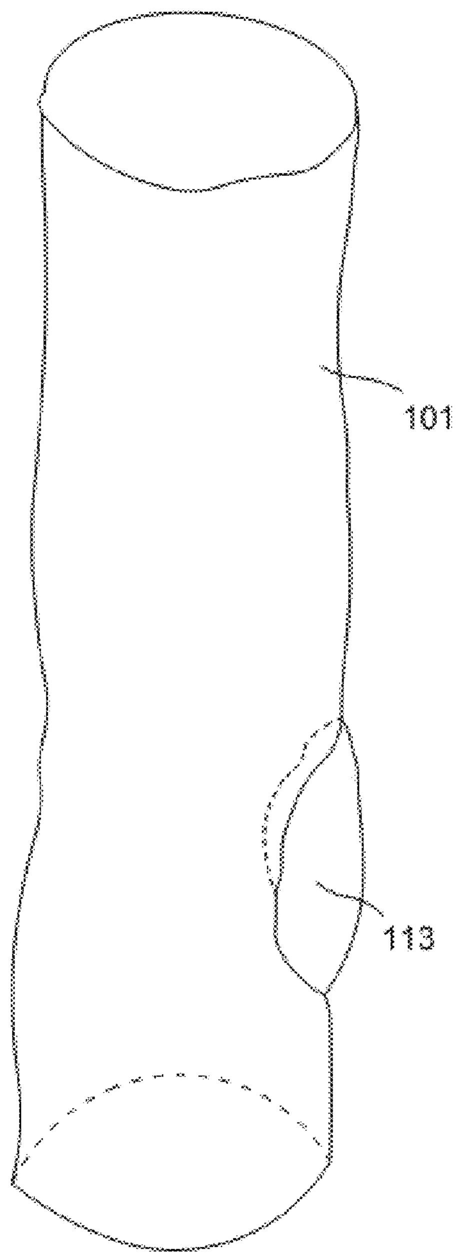
FIG. 7 illustrates a segment of a blood vessel.
Figure 8:
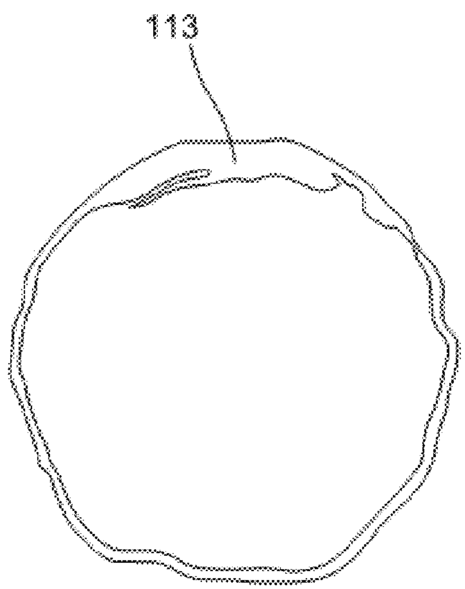
FIG. 8 illustrates a section of the blood vessel.

FIG. 7 provides an illustration of a segment of a vessel 101 having a feature 113 of interest. FIG. 8 shows a cross-section of vessel 101 through feature 113. In certain embodiments, intravascular imaging involves positioning imaging catheter 826 within vessel 101 near feature 113 and collecting data to provide a three-dimensional image. Data can be collected in three dimensions by rotating catheter 826 around a catheter axis to collect image data in radial directions around the catheter while also translating catheter 826 along the catheter axis. As a result of combined rotation and translation, catheter 826 collects image data from a series of scan lines (each referred to as an A-scan line, or A-scan) disposed in a helical array.

Figure 9:
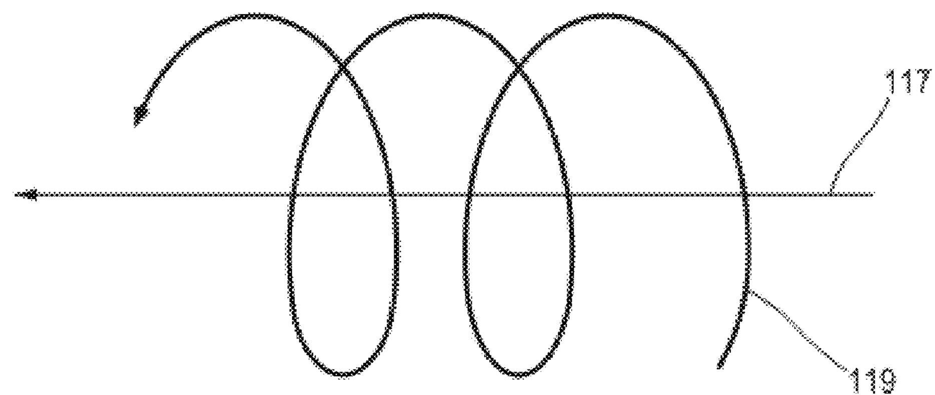
FIG. 9 shows the motion of parts of an imaging catheter.

FIG. 9 shows the motion of parts of an imaging catheter according to certain embodiments of the invention. Rotation of imaging catheter 826 around axis 117 is driven by spin motor 861 while translation along axis 117 is driven by pullback motor 865, as discussed above with reference to FIG. 4. An imaging tip of catheter 826 generally follows helical trace 119, resulting in a motion for image capture described by FIG. 9. Blood in the vessel is temporarily flushed with a clear solution for imaging. When operation is triggered from PIM 839 or a control console, the imaging core of catheter 826 rotates while collecting image data, which data is delivered to the imaging system.

Figure 10:
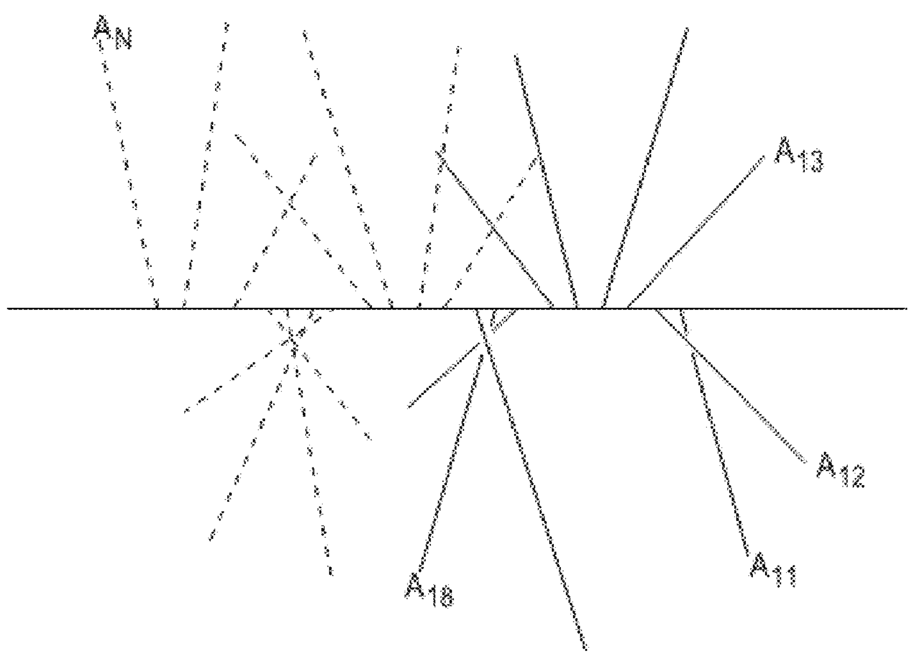
FIG. 10 shows an array of A scan lines of a three-dimensional imaging system.

FIG. 10 illustrates the helical array of A-scan lines $A_{11}$, $A_{12}$, . . . , $A_N$ captured by the imaging operation.

Figure 11:
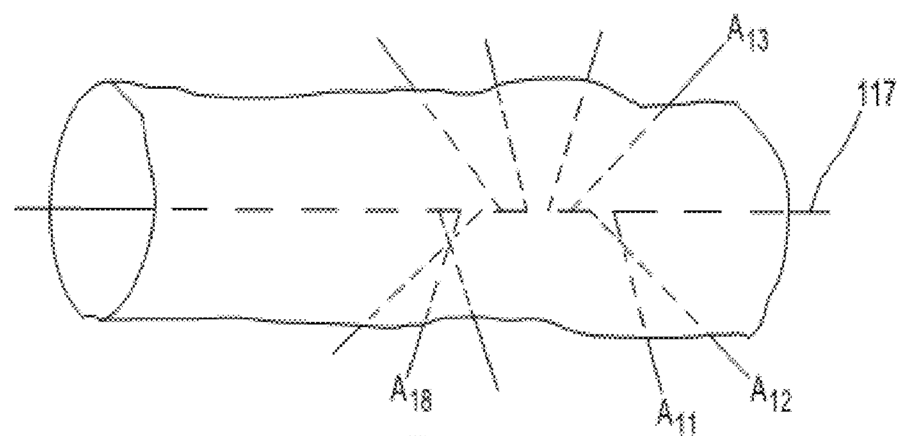
FIG. 11 shows the positioning of A scans with in a vessel.

FIG. 11 is provided to show the positioning of A-scans $A_{11}$, $A_{12}$, . . . , $A_N$ within vessel 101. Each place where one of A-scans $A_{11}$, $A_{12}$, . . . , $A_N$ intersects a surface of a feature within vessel 101 (e.g., a vessel wall) coherent light is reflected and detected. Catheter 826 translates along axis 117 being pushed or pulled by pullback motor 865.

Looking back at FIG. 6, the reflected, detected light is transmitted along sample path 913 to be recombined with the light from reference path 915 at splitter 919. Calibration of the system relates to a length of sample path 913 compared to a length of reference path 915. The difference between these lengths is referred to as the z-offset and when the paths are the same length, the z-offset is said to be zero, and the system is calibrated. Calibration will be discussed in more detail below. Z-offset is discussed in U.S. Pat. No. 8,116,605, the contents of which are hereby incorporated by reference in their entirety for all purposes. When the z-offset is zero, the system is said to be calibrated.

After combining light from the sample, and reference paths, the combined light from splitter 919 is split into orthogonal polarization states, resulting in RF-band polarization-diverse temporal interference fringe signals. The interference fringe signals are converted to photocurrents using PIN photodiodes 929*a*, 929*b*, . . . on the OCB 851 as shown in FIG. 6. The interfering, polarization splitting, and detection steps are done by a polarization diversity module (PDM) on the OCB. Signal from the OCB is sent to the DAQ 855, shown in FIG. 5. The DAQ includes a digital signal processing (DSP) microprocessor and a field programmable gate array (FPGA) to digitize signals and communicate with the host workstation and the PIM. The FPGA converts raw optical interference signals into meaningful OCT images. The DAQ also compresses data as necessary to reduce image transfer bandwidth to 1 gigabit per second (Gbps) (e.g., compressing frames with a lossy compression JPEG encoder).

Data is collected from A-scans $A_{11}$, $A_{12}$, . . . , $A_N$, as shown in FIG. 11, and stored in a tangible, non-transitory memory. A set of A-scans captured in a helical pattern during a rotation and pullback event can be collected and viewed alongside one another in a plane, in a format known as a B-scan.

Figure 12:
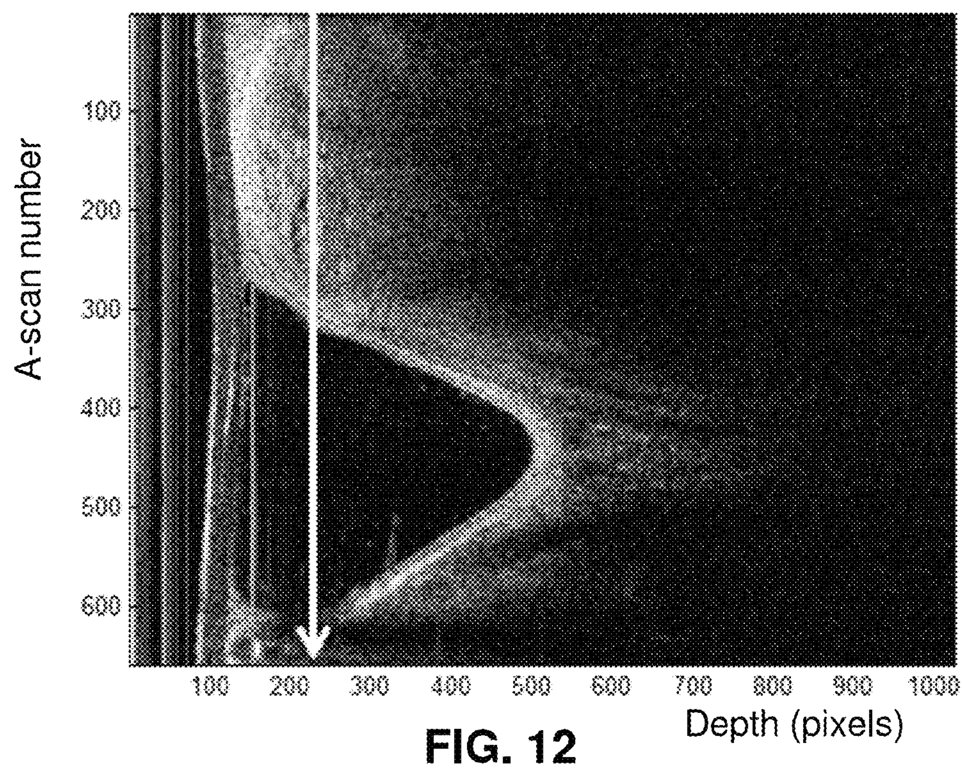
FIG. 12 shows a B-scan.

FIG. 12 gives a reproduction of a B-scan collected using an OCT system. Each horizontal row of pixels corresponds to one A-scan, with the first A-scan (e.g., $A_{11}$) being displayed across the top of the image. The horizontal axis labeled "Depth" represents a radial distance from imaging catheter 826. Noting—as shown in FIG. 10—that each A-scan line is progressively displaced from an adjacent A-scan in an angular direction around an axis 117 of catheter 826 (while also being displaced in a translational direction along axis 117), one set of A-scans associated with a 360° displacement around axis 117 can be collected into a view that depicts a slice of vessel 101 perpendicular to axis 117. This view is referred to as a tomographic view.

Figure 13:
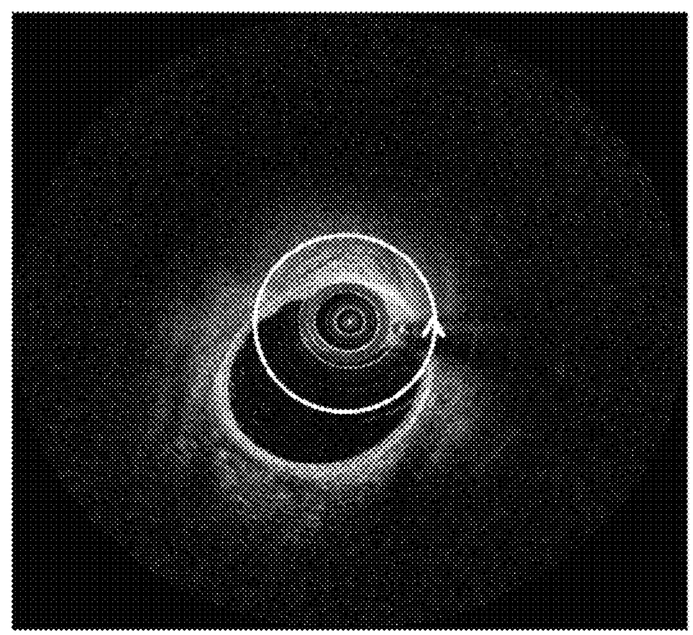
FIG. 13 shows a tomographic view based on the B-scan of FIG. 11.

FIG. 13 shows a tomographic view based on the B-scan of FIG. 11. A tomographic view comprises a set of A-scans that defines one circumference around vessel 101. An arrow pointing straight down in FIG. 12 corresponds to the circular arrow in FIG. 13 and aids in visualization of the three-dimensional nature of the data.

Figure 14:
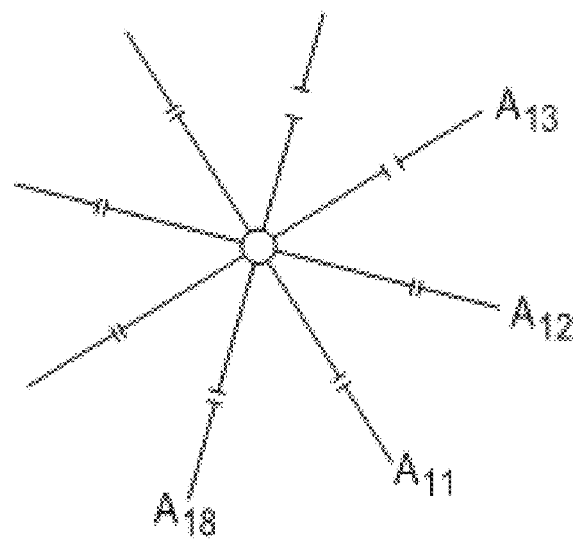
FIG. 14 illustrates a set of A scans used to compose a tomographic view.

FIG. 14 provides a cartoon illustration of a set of A-scans $A_{11}$, $A_{12}$, . . . , $A_{18}$ used to compose a tomographic view. These A-scan lines are shown as would be seen looking down axis 117 (i.e., longitudinal distance between them is not shown). While eight A-scan lines are here illustrated in cartoon format in FIG. 14, typical OCT applications can include between 300 and 1,000 A-scan lines to create a B scan (e.g., about 660) or a tomographic view.

Figure 15:
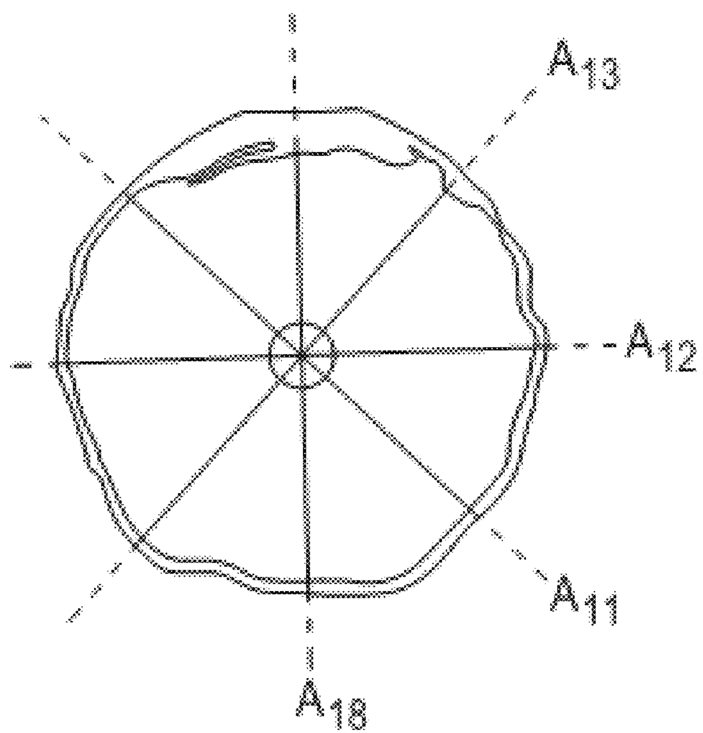
FIG. 15 shows the set of A scans shown in FIG. 14 within a cross section of a vessel.

FIG. 15 provides a cartoon illustration of the tomographic view associated with the A-scans of FIG. 14. Reflections detected along each A-scan line are associated with features within the imaged tissue. Reflected light from each A-scan is combined with corresponding light that was split and sent through reference path 915 and VDL 925 and interference between these two light paths as they are recombined indicates features in the tissue. Where a tomographic view such as is depicted in FIG. 15 generally represents an image as a planar view across a vessel (i.e., normal to axis 117), an image can also be represented as a planar view along a vessel (i.e., axis 117 lies in the plane of the view).

Figure 16:
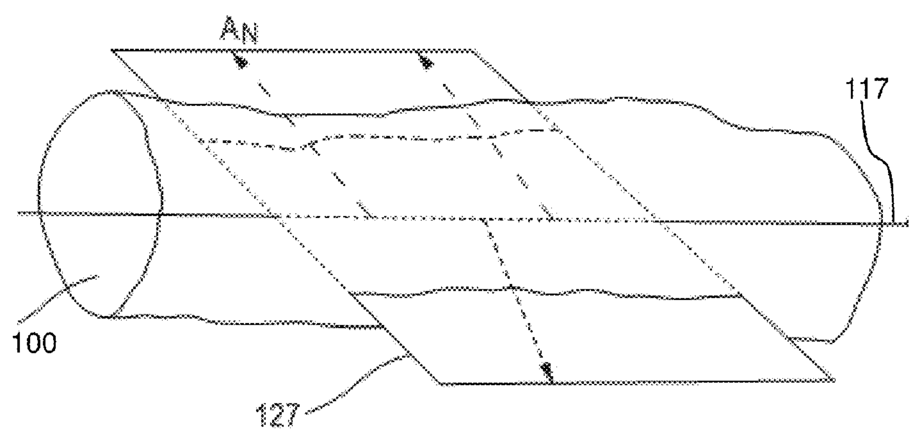
FIG. 16 shows a longitudinal plane through a vessel including several A scans.

FIG. 16 shows a longitudinal plane 127 through a vessel 101 including several A scans. Such a planar image along a vessel is sometimes referred to as an in-line digital view or image longitudinal display (ILD). As shown in FIG. 16, plane 127 generally comprises data associated with a subset of the A scans. The data of the A scan lines is processed according to systems and methods of the inventions to generate images of the tissue. By processing the data appropriately (e.g., by fast Fourier transformation), a two-dimensional image can be prepared from the three dimensional data set. Systems and methods of the invention provide one or more of a tomographic view, ILD, or both.

Figure 17:
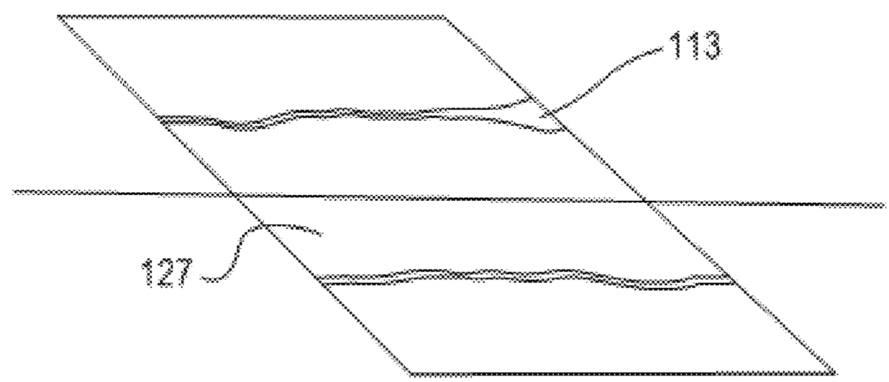
FIG. 17 is a perspective view of an image longitudinal display (ILD) of FIG. 16.

FIG. 17 is a perspective view of an idealized plane shown including an exemplary ILD in the same perspective as the longitudinal plane shown in FIG. 16. Where an OCT system captures three-dimensional image data, host workstation 433 may store the three dimensional image data in a tangible, non-transitory memory and provides a display that includes a tomographic view (e.g., FIG. 15), an ILD (e.g., FIG. 17), or both (e.g., on a screen or computer monitor). In some embodiments, a tomographic view and an ILD are displayed together, providing information that operators can intuitively visualize as representing a three-dimensional structure.

Figure 18:
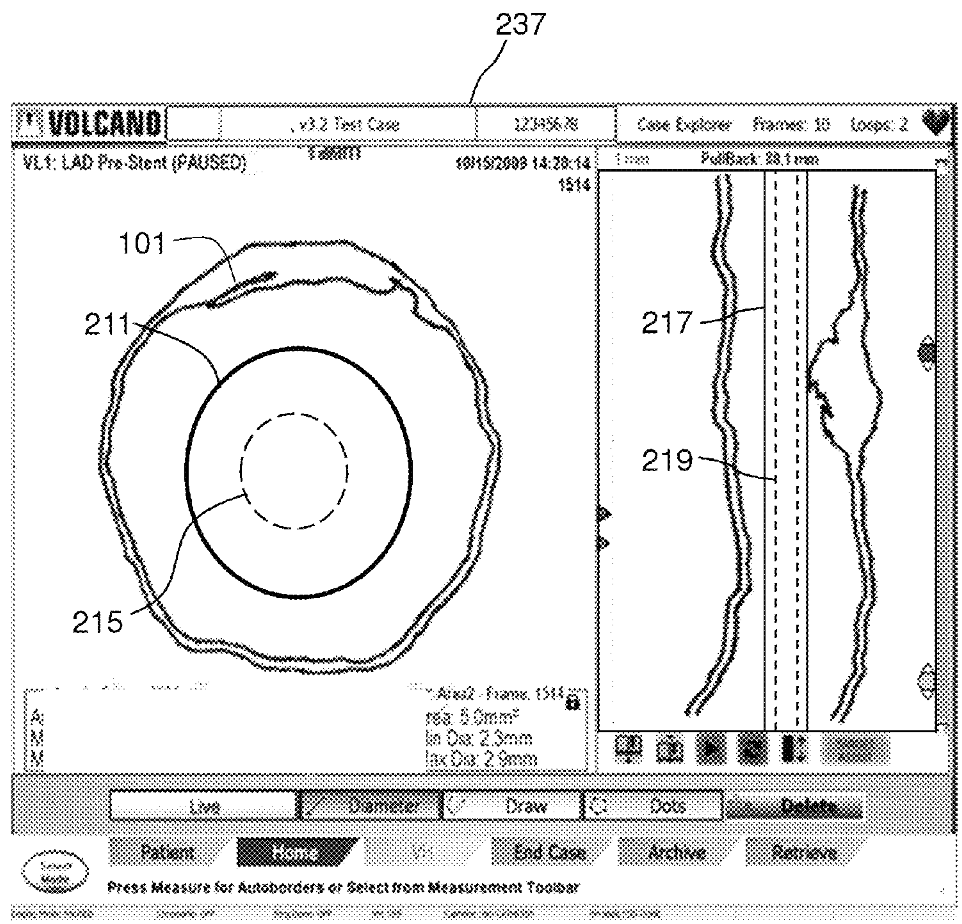
FIG. 18 is a display providing an image of the vessel shown in FIGS. 7 and 8.

FIG. 18 is a reproduction of a display of an OCT system including a tomographic view on the left and an ILD on the right. As shown in FIG. 18, a tomographic view may include ring-like elements near the center and the ILD may include corresponding sets of vertical line-like elements. One ring in the tomographic view may correspond to one pair of lines in the ILD. These elements within the displays are often, in-fact, images of part of the imaging system itself. In some embodiments, a ring in a tomographic view and lines in an ILD represent a surface of catheter 826 such as, for example, an outer surface of a catheter sheath. The portions of the images extending away from those elements are the images of the patient's tissue.

The invention provides methods and systems for detecting and using OCT image features, either intentionally generated or artifactual, for automatically adjusting the depth range in polar ("radar-like") OCT images. Circular or cylindrical OCT scanning devices sample physical space in an inherently polar coordinate system (e.g. radius and angle rather than length and width). However, digital representations of images (i.e. arrays of pixels representing numeric values) are inherently rectangular as shown in FIG. 12.

Polar OCT images must be converted from their rectangular representation (from FIG. 12) before displaying to the viewer (e.g., transformed to FIG. 13). Additionally, if quantitative values (e.g. lumen diameters, lumen areas, circumferences, etc.) are to be measured on the polar image, then the transformation from rectangular to polar must preserve relative distances between pixels in all dimensions (radial and angular). Generally, the OCT depth scan (y axis in rectangular coordinates) maps directly to radius and the OCT circumferential scan (x axis in rectangular coordinates) maps to some increment of 2π radians (or 360°) polar angle.

For example: y=0 (the top row of the rectangular image) maps to radius=0 (the center of the polar image) and y=ymax (the bottom row of the rectangular image) maps to radius=ymax (the perimeter of the polar image). Likewise, x=0 (the left column in the rectangular image) maps to angle=0° and x=xmax/2 maps to approximately 180° and x=xmax maps to an angle of approximately 359°. (It is noted that the assignment of x or y to rows or columns is arbitrary and non-limiting. Herein, "x" and "y" could be reversed in any example, meaning only that a rectangular image would be stored in the computer memory as a transpose relative to the other.)

For accurate quantitative dimensional measurement in polar images, pixels mapping to radius=0 must represent the actual physical space at the center of the axis of rotation of the imaging probe, otherwise the polar image will be artificially warped (expanded or contracted) in the radial direction. However, in an arbitrary OCT image, the pixels at y=0 do not necessarily satisfy this requirement and must be shifted in the y dimension until this is satisfied before mapping to a polar representation. Differential displacements (either controlled or uncontrolled) in the path length of the sample vs. reference arms of the interferometer will shift the pixels in the y dimension.

Displacements can occur when using cylindrical (typically actually helical) scanning fiber-optic OCT catheters. For example, when the catheter is pushed or pulled longitudinally, the fiber-optic cable can be compressed or stretched and thus a path length displacement is incurred.

The method disclosed herein is of automatic recognition of the uncontrolled displacement effect based on searching for image features which should be stationary (but are not due to uncontrollable displacement), and successive calibration of OCT image data so that polar representations can then be used for accurate dimensional measurements.

Additionally, a method is provided for subsequent removal of said features in image prior to display.

Image features used by the methods and systems disclosed herein are preferably generated within the catheter itself (i.e., not within the imaged subject or surroundings) and should appear somewhat stable in depth and consistent in intensity throughout the 360° rotation of the catheter. These include but are not limited to back reflections at interfaces between optical components (aka "ghost-lines" or "echo artifacts", these occur along the optical axis of rotating parts and thus appear as uniform circles in the polar image when no differential path length displacement occurs over the course of one catheter rotation), or reflections from the boundaries of or from within the stationary (non-rotating) catheter sheath (if it is circular in cross-sectional profile and also mechanically concentric with the rotating portion).

In some embodiments, steps in the automatic recognition and calibration method could include first averaging an OCT image frame along the x—(i.e. angular) dimension. This selectively enhances the feature(s) which are rotationally stable in the y dimension (i.e. radius) instead of other image features generated by subject or surroundings. Efficacy of the method is improved if the image feature(s) used have high intensity relative to the surrounding pixels and if subject/environment features (noise) do not have strong circumferential symmetry.

Next, features can be detected within the image. Features can be found by any suitable method or algorithm such as, for example, peak searching, correlation, thresholding, or other pattern recognition algorithms known in the art. The efficacy of this method can be improved if the range over which uncontrolled path length displacements can occur is known a priori, thus limiting the required search space.

Then, the y-value(s) of feature(s) found in the previous step are compared to a pre-calibrated y-value which represents the actual physical location(s) of that feature(s) relative to the rotational axis, or to the location of a known "conjugate image" or "aliased image" of that feature(s) when using spectral-domain OCT.

Finally, the image is calibrated by shifting the OCT image pixels in the y dimension by the difference between searched feature(s) and pre-calibrated feature(s). Multiple features can be used to improved efficacy of the algorithm. After shifting the rectangular image in the y dimension, map to polar image coordinates. Radii measured to the center of the calibrated polar image will represent actual radii measured to the rotational axis in physical space.

Often image features due to the catheter are unwanted for effective and distraction-free display of the subject/environment features. For example, the catheter image features could overlap the subject/environment features.

Steps to remove (or make less noticeable) the image features could include cropping out the image feature(s) extent in the y, or radial, direction and in all columns, or angles. Removal (or diminishment) can further include calculating the average value of the pixels immediately inside and outside (above and below) of the cropped region for all columns, or angles, and inserting this averaged row, or circumference, in the cropped location.

FIG. 18 is a cartoon illustration of a display 237 including an image of the vessel shown in FIGS. 7 and 8, as rendered by a system of the invention. The images included in display 237 in FIG. 18 are rendered in a simplified style of the purposes of ease of understanding. A system of the invention may render a display as shown in FIG. 18, or in any style known in the art (e.g., with or without color).

As shown in FIG. 18, a tomographic view of vessel 101 is depicted alongside an ILD. An outer surface of a catheter sheath appears as a ring 211 in the tomographic view and as lines 217 in the ILD. The tomographic view is depicted as including calibration mark 215, while calibration mark 219 appears in the ILD.

Figure 19:
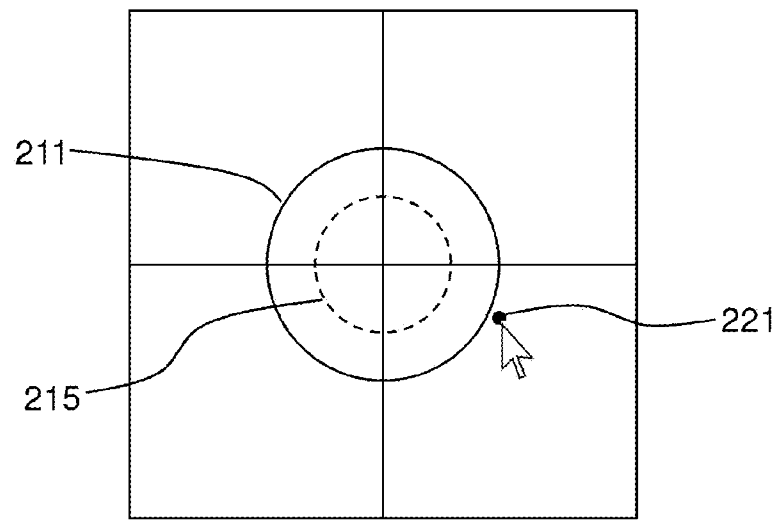
FIG. 19 illustrates receiving user input indicating a point within an image.

In some embodiments, calibration involves determining the position of ring 211 (or lines 217) in display 237 so that the system can calculate a calibration value based on a known position of calibration mark 215 (see FIG. 19; calibration mark 215 need not ever be a visible mark—it represents a conceptual point). Systems of the invention can determine the position of ring 211 or any other calibration element based on an image processing operation.

FIG. 19 illustrates, in simplified fashion, a display of an imaging system showing a catheter sheath 211 and calibration mark 215.

The system can additionally use a processor to perform an image processing operation to detect a feature such as sheath 211.

In some embodiments, the system detects a feature by starting with a defined area 227 (e.g., a pre-stored range of search values, or an arbitrary area, or the entire image).

Figure 20:
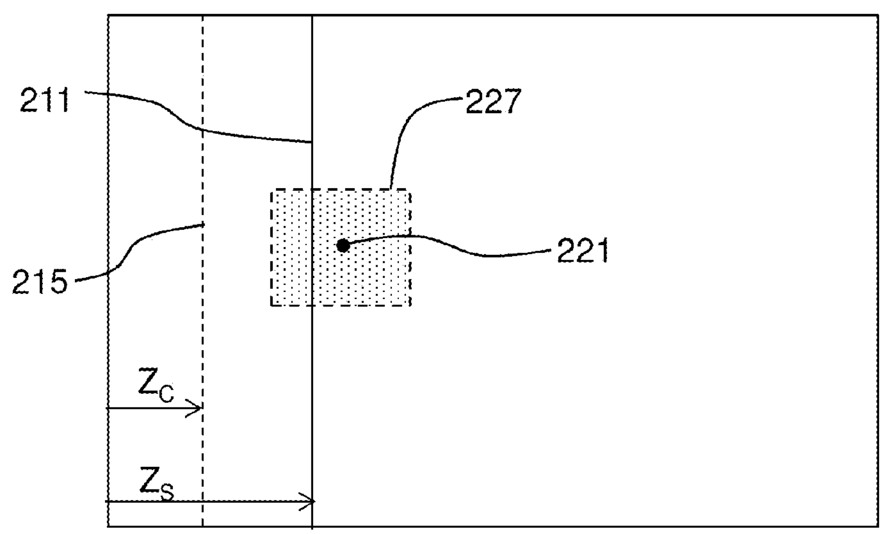
FIG. 20 shows an area around a point to be searched.

FIG. 20 depicts a defined area 227 around point 221 on a B-scan. Area 227 operates as a search window. The search window area 227 may be a rectangle, circle, ellipse, polygon, or other shape. It may have a predetermined area (e.g., a certain number of pixels). In some embodiments, a size and shape of area 227 is determined by a prior information about a likely location of a feature to be detected.

The system searches for a feature (e.g., a sheath) within area 227 by performing a processing operation on the corresponding data. The processing operation can be any suitable search algorithm known in the art.

In some embodiments, a morphological image processing operation is used. Morphological image processing includes operations such as erosion, dilation, opening, and closing, as well as combination thereof. In some embodiments, these operations involve converting the image data to binary data giving each pixel a binary value. With pixels within area 227 converted to binary, each pixel of catheter sheath 211 will be black, and the background pixels will predominantly be white. In erosion, every pixel that is touching background is changed into a background pixel. In dilation, every background pixel that is adjacent to the non-background object pixels is changed into an object pixel. Opening is an erosion followed by a dilation, and closing is a dilation followed by an erosion. Morphological image processing is discussed in Smith, The Scientist and Engineer's Guide to Digital Signal Processing, 1997, California Technical Publishing, San Diego, Calif., pp. 436-442.

If sheath 211 is not found within area 227, area 227 can be increased and the increased area can be searched. This strategy can exploit the statistical properties of signal-to-noise ratio (SNR) by which the ability to detect an object is proportional to the square root of its area. See Smith, Ibid., pp. 432-436.

With continued reference to FIG. 20, once a portion of catheter sheath 211 is detected within area 227, the search can then be extended "upwards" and "downwards" into adjacent A-scan lines in the B-scan until the entire catheter sheath 211 is detected by the processor and its location is determined with precision. In some embodiments, image processing operations incorporate algorithms with pre-set or user-set parameters that optimize results and continuity of results. For example, if a line appears that is not contiguous across an entire 100% of the image (e.g., the entire extent of the B-scan or a full circle in a tomographic view), an accept or reject parameter can be established based on a percent contiguous factor. In some embodiments, lines that are contiguous across less than 75% (or 50% or 90%, depending on applications) are rejected while others are accepted.

While described above as detecting a reference item (e.g., catheter sheath 211) by receiving user input followed by using a processor to detect a location of the sheath, the steps can be performed in other orders. For example, the system can apply morphological processing operations to an entire image and detect every element, or every element that satisfies a certain quality criterion. In some embodiments, the system can receive user input that indicates a point within an image and the user can then choose the pre-detected element that is closest to that point within the image. Similarly, the steps can be performed simultaneously.

Using the methodologies herein, systems of the invention can detect an element within an image of an imaging system, such as an OCT system, with great precision, based on a search algorithm. Based on this detection, an actual location of a catheter sheath is determined and thus a precise calibration value for the catheter sheath and thus for the image (e.g., within a B-scan) is known. Where an expected z-coordinate $Z_c$ for the catheter sheath is known, based on information provided extrinsically, the a calibration value can be determined. For example, in FIG. 20, $Z_s$ is depicted as lying to the right of $Z_c$, thereby showing a non-zero z-offset. The calibration value is then used to provide a calibrated image, or an image at a known scale.

In some embodiments, the system calculates or uses the mean, median, or root-mean-squared distance of the sheath from the calibration mark to compute the calibration value. This may be advantageous in the event of interfering speckle noise, rough or acylindrical sheaths, non-uniform catheter rotation (NURD), angular displacement of a transducer within the sheath, off-center positioning of the transducer within the sheath, or a combination thereof. In certain embodiments, only a subset of the detected points are used, for example, for efficiency or performance optimization.

Figure 21:
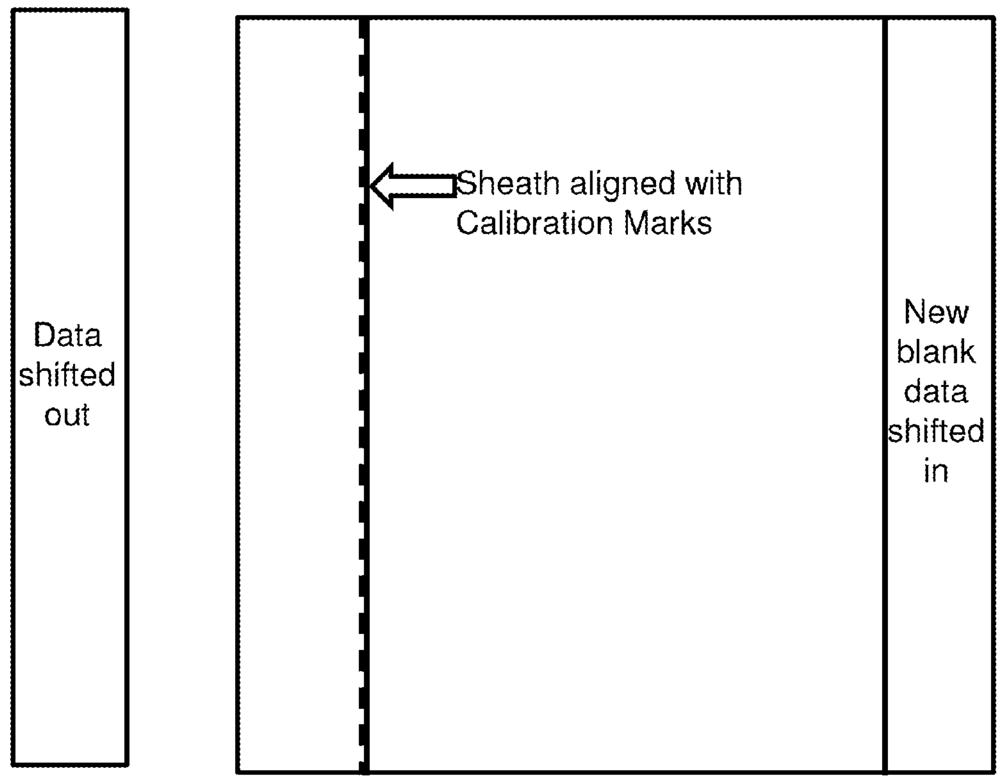
FIG. 21 shows a calibrated B-scan.

FIG. 21 shows a calibrated image, here, a B-scan. The image is depicted having the catheter sheath aligned with the calibration mark. Bars on the left and right side of FIG. 21 show that some data may be shifted out and some blank space introduced by the calibration. In an alternative embodiment, the image can be stretched or compressed, or a combination of stretching and shifting may be performed, depending on preferences, purposes, or functions of a system.

It will be appreciated that the foregoing description is applicable in live mode or review mode. If the imaging system is operating in live mode, capturing an image of tissue, the calibration can be put into effect either by changing the length of reference path 915 so that z-offset is zero or by transforming the dataset or on-screen image. The length of reference path 915 can be changed through the operation of the motor in the VDL. The distance $Z_c$-$Z_s$ is converted into millimeters and the a command is sent to move the VDL to a new position.

If the dataset is to be transformed, either in live mode or while the system is operating in review mode, the system is digitally shifted, stretched, or a combination thereof.

In another aspect, the invention provides a method for calibrating an imaging system based on receipt of user input that indicates a “motion”, such as a click-and-drag operation on a computer screen.

While discussed above using a surface of a catheter sheath as a reference item which is used as a basis for calibration, other reference items are suitable. For example, any item that can be depicted such that its expected location and actual location can be compared in a display of an imaging system may be used. In some embodiments, a fiducial marker or calibration bar is introduced into the imaging target having a known dimension (e.g., 1 nm, 1 mm, 1 cm). The system operates to display a scale or a grid based on an expected appearance of the known dimension. The user then gives input indicating a point in the display near the reference item and the system also detects a location of the reference item in an area around the indicated point. Based on the expected and actual locations or dimensions of the reference item, a calibration value is calculated and a calibrated image is provided. User input, displays, and methods of receiving user input and performing calculations may be provided by one or more computers.

In certain embodiments, display 237 is rendered within a computer operating system environment, such as Windows, Mac OS, or Linux or within a display or GUI of a specialized system. Display 237 can include any standard controls associated with a display (e.g., within a windowing environment) including minimize and close buttons, scroll bars, menus, and window resizing controls. Elements of display 237 can be provided by an operating system, windows environment, application programming interface (API), web browser, program, or combination thereof (for example, in some embodiments a computer includes an operating system in which an independent program such as a web browser runs and the independent program supplies one or more of an API to render elements of a GUI). Display 237 can further include any controls or information related to viewing images (e.g., zoom, color controls, brightness/contrast) or handling files comprising three-dimensional image data (e.g., open, save, close, select, cut, delete, etc.). Further, display 237 can include controls (e.g., buttons, sliders, tabs, switches) related to operating a three dimensional image capture system (e.g., go, stop, pause, power up, power down).

In certain embodiments, display 237 includes controls related to three dimensional imaging systems that are operable with different imaging modalities. For example, display 237 may include start, stop, zoom, save, etc., buttons, and be rendered by a computer program that interoperates with OCT or IVUS modalities. Thus display 237 can display an image derived from a three-dimensional data set with or without regard to the imaging mode of the system.

Figure 22:
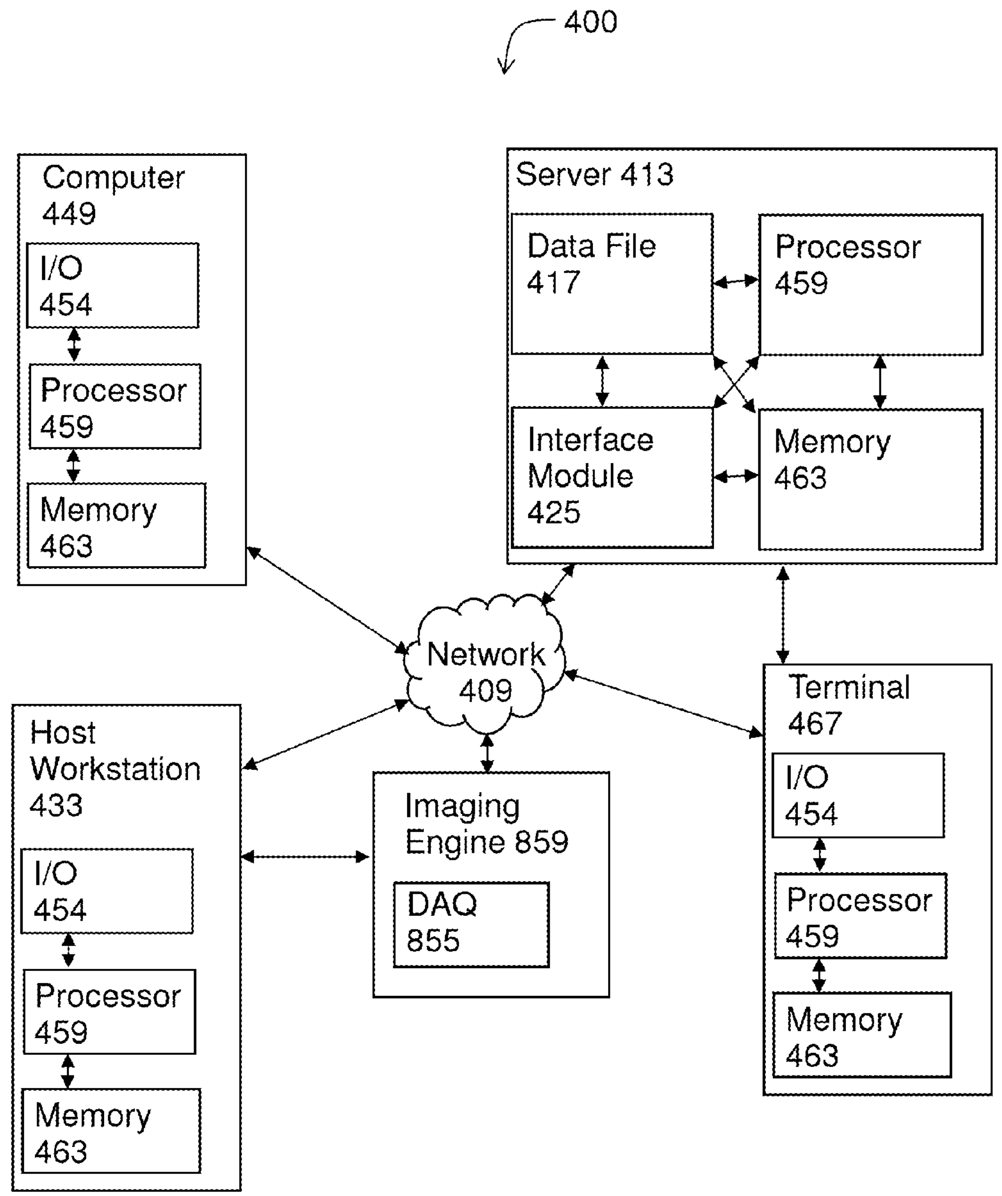
FIG. 22 illustrates components of a system according to certain embodiments.

FIG. 22 diagrams an exemplary system 400. As shown in FIG. 22, imaging engine 859 communicates with host workstation 433 as well as optionally server 413 over network 409. In some embodiments, an operator uses host workstation 433, computer 449, or terminal 467 to control system 400 or to receive images. An image may be displayed using an I/O 454, which may include a monitor. Any I/O may include a monitor, keyboard, mouse or touchscreen to communicate with any of processor 459, for example, to cause data to be stored in any tangible, nontransitory memory 463. Server 413 generally includes an interface module 425 to communicate over network 409 or write data to data file 417. Input from a user is received by a processor in an electronic device such as, for example, host workstation 433, server 413, or computer 449. Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections). In certain embodiments, host workstation 433 and imaging engine 855 are included in a bedside console unit to operate system 400.

A computer generally includes a processor for executing instructions and one or more memory devices for storing instructions, data, or both. Processors suitable for the execution of methods and operations described herein include, by way of example, both general and special purpose microprocessors (e.g., an Intel chip, an AMD chip, an FPGA). Generally, a processor will receive instructions or data from read-only memory, random access memory, or both. Generally, a computer will also include, or be operatively coupled, one or more mass storage devices for storing data that represent target such as bodily tissue. Any suitable computer-readable storage device may be used such as, for example, solid-state, magnetic, magneto-optical disks, or optical disks. Information carriers suitable for embodying computer program instructions and data include all forms of non-volatile memory, particularly tangible, non-transitory memory including by way of example semiconductor memory devices, (e.g., EPROM, EEPROM, NAND-based flash memory, solid state drive (SSD), and other flash memory devices); magnetic disks, (e.g., internal hard disks or removable disks); magneto-optical disks; and optical disks (e.g., CD and DVD disks).

Incorporation By Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method of calibrating an imaging system, the method comprising: using the processor for;

obtaining an image that includes a target and a reference item;

detecting a location of the reference item within the image;

determining a y-value of the location;

comparing the determined y-value to a stored reference y-value;

calculating a calibration value based on the comparison; and providing a calibrated image by shifting pixels in a y-direction according to the calibration value;

wherein calculating the calibration value comprises taking a difference between the determined y-value and the stored reference y-value.

2. The method of claim 1, wherein the pixels are shifted by the difference.

3. A method of calibrating an imaging system, the method comprising: using the processor for;

obtaining an image that includes a target and a reference item;

detecting a location of the reference item within the image;

determining a y-value of the location;

comparing the determined y-value to a stored reference y-value;

calculating a calibration value based on the comparison;

providing a calibrated image by shifting pixels in a y-direction according to the calibration value; and removing a feature from the image;

wherein removing comprises cropping out the feature across its extent in the y direction at all x positions.

4. The method of claim 3, wherein removing comprises calculating an average value of pixels proximal to the cropped region and inserting the average values to replace the cropped pixels.

* * * * *